(12) United States Patent
Qu et al.

(10) Patent No.: US 8,367,737 B2
(45) Date of Patent: Feb. 5, 2013

(54) METHOD OF USING BIOTHIONOL AND BIOTHIONOL-LIKE COMPOUNDS AS ANTI-ANGIOGENIC AGENTS

(75) Inventors: Zhican Qu, Birmingham, AL (US);
Anshu M. Roy, Rajasthan (IN);
Subramaniam Ananthan, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 12/595,278

(22) PCT Filed: Apr. 14, 2008

(86) PCT No.: PCT/US2008/060186
§ 371 (c)(1),
(2), (4) Date: Apr. 12, 2010

(87) PCT Pub. No.: WO2009/023299
PCT Pub. Date: Feb. 19, 2009

(65) Prior Publication Data
US 2010/0204338 A1 Aug. 12, 2010

Related U.S. Application Data

(60) Provisional application No. 60/911,645, filed on Apr. 13, 2007.

(51) Int. Cl.
*A01N 31/00* (2006.01)
*A61K 31/10* (2006.01)

(52) U.S. Cl. .................................................. 514/712

(58) Field of Classification Search ........................ None
See application file for complete search history.

(56) References Cited

U.S. PATENT DOCUMENTS

| | | | | |
|---|---|---|---|---|
| 5,635,351 A | * | 6/1997 | Feuerstein et al. | 435/6 |
| 2004/0077601 A1 | * | 4/2004 | Adams et al. | 514/64 |
| 2005/0250709 A1 | | 11/2005 | Khodadoust | |
| 2005/0266510 A1 | | 12/2005 | Gajewski | |
| 2006/0018934 A1 | | 1/2006 | Vaya et al. | |
| 2007/0225238 A1 | | 9/2007 | Charlier | |

FOREIGN PATENT DOCUMENTS

| | | |
|---|---|---|
| WO | WO-91/02527 A1 | 3/1991 |
| WO | WO-92/04014 A2 | 3/1992 |
| WO | WO-0045165 A1 | 8/2000 |
| WO | WO-02/060375 A2 | 8/2002 |
| WO | WO-03/070249 A1 | 8/2003 |
| WO | WO-03070249 A1 | 8/2003 |
| WO | WO-03/106660 A2 | 12/2003 |
| WO | WO-2004/061408 A2 | 7/2004 |
| WO | WO-2007005670 A2 | 1/2007 |
| WO | WO-2007041409 A1 | 4/2007 |
| WO | WO-2008/090334 A1 | 7/2008 |

OTHER PUBLICATIONS

Kim et al. Treatment of Microcotyle sebastics (Monogenea) on the gills of cultured rockfish (*Sebastes schelegeli*) with oral administration of mebendazole and bithionol. Aquaculture, 167, 115-121, 1998).*
Vippagunta et al. Advanced Drug Reviews, 48, 2001.*
Stella et al. (Prodrugs: Challenges and Rewards, Part 1, 2007).*
Newton (Exp. Opin. Invest. Drugs, 2000, 9(12): 2815-2829).*
Robertson J I S: "Serotonergic type-2w (5-HT2) antagonists: A novel class of cardiovascular drugs," Journal of Cardiovascular Pharmacology, Raven Press, New York NY, vol. 17, No. Supplement S, Jan. 1, 1991, pp. S48-S53.
Taylor, Andrew J. et al.: "Serotonin blockade protects against early microvascular constriction following athrosclerotic plaque rupture," European Journal of Pharmacology, vol. 486, No. 1, Feb. 13, 2004, pp. 85-89.
Partial European Search Report issued in related European Application No. 09178514.7 on Aug. 13, 2010.
International Search Report of International Publ. No. WO2009/023299 dated Mar. 30, 2009.
Xu et al.; "Polybrominated Diphenyl Ethers from a Sponge fo the Dysidea Genus that Inhibit Tie2 Kinase," Bioorganic & Medicinal Chemistry, Pergamon, GB, vol. 13, No. 3, Feb. 1, 2005, pp. 657-659.
Database CA, Chemical Abstracts Service, Columbus, Ohio, US; Oct. 12, 2005, Yao et al., Extraction of Derivatives of Polyhalogenated Diphenyl Ethers from *Phyllospongia* and their Medical Applications.
Liu et al.; "Triclosan Inhibits Enoyl-Reducatase of Type I Fatty Acide Synthase in Vitro and is Cytotoxic to MCF-7 and SKBr-3 Breast Cancer Cells," Cancer Chemotherapy and Pharmacology, vol. 49, No. 3, Mar. 1, 2002.
Lu; "Fatty Acid Synthase is a Potential Molecular Target for the Chemoprevention of Breast Cancer," Carcinogenesis, vol. 26, No. 1, Jan. 1, 2004, pp. 153-157.
Williams et al.; "Inhibitors of Human Carbonyl Reductase," Journal of the Idaho Academy of Science, Jun. 2005.
Extended European Search Report issued in related European Application No. 08827229.9 on Aug. 18, 2011.

* cited by examiner

*Primary Examiner* — Brandon Fetterolf
*Assistant Examiner* — Anna Pagonakis
(74) *Attorney, Agent, or Firm* — Connolly Bove Lodge & Hutz LLP

(57) ABSTRACT

The present disclosure relates generally to treating or preventing diseases associated with angiogenesis by administering to a patient certain compounds found to inhibit or substantially reduce angiogenesis. Compounds employed according to the present disclosure exhibit good anti-angiogenic activity as well as demonstrate a prophylactic effect for preventing and substantially reducing angiogenesis. Examples of such compounds include Ritanserin, Amiodarone, Terfenadinc, Perphenazine, Bithionol, and Clomipramine.

3 Claims, 25 Drawing Sheets

Ritanserin Xenograft Mouse Model

| Animal Group | # of mice | Tumor Line | Treatment (Start on Day 0) | Dose mg/kg (i.p. injection everyday) | Inhibition tumor size |
|---|---|---|---|---|---|
| 1 | 10 | MX-1 | Vehicle | - | - |
| 2 | 6 | MX-1 | Ritanserin | 1.2 – 2.4 – 4.8 | 40% |
| 3 | 10 | SKOV-3 | Vehicle | - | - |
| 4 | 6 | SKOV-3 | Ritanserin | 1.2 – 2.4 – 4.8 | 41% |

METHOD OF USING BIOTHIONOL AND BIOTHIONOL-LIKE COMPOUNDS AS ANTI-ANGIOGENIC AGENTS

CROSS REFERENCE TO RELATED APPLICATIONS

This application is a National Phase filing under 35 U.S.C. §371 of PCT/US2008/060186 filed Apr. 14, 2008, which claims priority under 35 U.S.C. §119(a) to U.S. Provisional Application No. 60/911,645 filed on Apr. 13, 2007. The entire contents of each of the above-applications are incorporated herein by reference.

TECHNICAL FIELD

The present disclosure relates generally to treating or preventing diseases associated with angiogenesis by administering to the patient certain compounds found to inhibit or substantially reduce angiogenesis. Compounds employed according to the present disclosure exhibit good anti-angiogenic activity as well as demonstrate a prophylactic effect in preventing and substantially reducing angiogenesis. Examples of such compounds include Ritanserin, Amiodarone, Terfenadine, Perphenazine, Bithionol, and Clomipramine.

BACKGROUND

Angiogenesis is the formation of new blood vessels out of pre-existing capillaries and is a sequence of events that is of key importance in many physiologic and pathologic processes. Normal tissue growth, such as in embryonic development, wound healing, and the menstrual cycle, is characterized by dependence on new vessel formation for the supply of oxygen and nutrients as well as removal of waste products. A large number of different and unrelated diseases are also associated with formation of new vasculature. Among certain pathologies are conditions in which angiogenesis is low, and should be enhanced to improve disease conditions. Pathologies which involve inadequate blood vessel formation include peripheral and coronary ischemia and infarction, chronic wound healing failure, and ulcer's. More frequently, however, excessive angiogenesis is an important characteristic of various pathologies including pathologies characterized or associated with an abnormal or uncontrolled proliferation of cells. Pathologies which involve excessive angiogenesis include, for example, cancer (both solid and hematologic tumors), cardiovascular diseases (such as atherosclerosis and restenosis), chronic inflammation (rheumatoid arthritis, Crohn's disease), diabetes (diabetic retinopathy), psoriasis, endometriosis, neovascular glaucoma and adiposity. See Griffioen & Molema, *Angiogenesis: Potentials for Pharmacologic Intervention in the Treatment of Cancer, Cardiovascular Diseases, and Chronic Inflammation*, PHARMACOL. REV. 52, 237-268 (2000).

Generally speaking, the angiogenic process entails the proliferation and migration of a normally quiescent endothelium, the controlled proteolysis of the pericellular matrix, and the synthesis of new extracellular matrix components by developing capillaries. The establishment of new intra- and intercellular contacts and the morphological differentiation of endothelial cells to capillary-like tubular networks provide support for their subsequent maturation, branching, remodeling and selective regression to form a highly organized, functional microvascular network. The autocrine, paracrine and amphicrine interactions of the vascular endothelium with its surrounding stromal components, as well as with the pro-angiogenic and angiostatic cytokines and growth factors orchestrating physiologic angiogenesis, are normally tightly regulated both spatially and temporally. See Gasparini, *The Rationale and Future Potential of Angiogenesis Inhibitors in Neoplasia*, DRUGS, 58(1):17-38 (1999)

The best known anti-angiogenic agents targeting endothelial cell proliferation are Vascular Endothelial Growth Factor ("VEGF") inhibitors. VEGF, a potent angiogenic growth factor, is over expressed in most human solid tumors and in the retina associated eye disorders. The VEGF receptors are mainly enriched in endothelial cells transducing VEGF signaling in many pathological angiogenesis conditions. Growth-stimulated endothelial cells are also sensitive to tyrosine kinase inhibitors targeting VEGF receptors, such as the recent FDA approved anti-cancer drugs Sunitinib (SU11248) and Srafenib (BAY 43-9006). Anti-VEGF and VEGF receptor agents are able to arrest endothelial cell proliferation and prevent new blood vessel growth. In addition to VEGF, many other growth factors such as fibroblast growth factors (FGFs) and platelet derived growth factors (PDGF) also play important roles in endothelial activation. Recently, resistance to anti-angiogenic agents targeting only VEGF signaling is emerging presumably due to other growth factor mediated alternative signaling pathways.

Angiogenesis is crucial to the growth of neoplastic tissues. For more than 100 years, tumors have been observed to be more vascular than normal tissues. Several experimental studies have suggested that both primary tumor growth and metastasis require neovascularization. In contrast to the well orchestrated process described above for normal tissue growth, the pathologic angiogenesis necessary for active tumor growth is generally sustained and persistent, with the initial acquisition of the angiogenic phenotype being a common mechanism for the development of a variety of solid and hematopoietic tumor types. See Folkman, J., CANCER MEDICINE, 132-152 (5th Ed., B.C. Decker Inc.) (2000). Tumors that are unable to recruit and sustain a vascular network typically remain dormant as asymptomatic lesions in situ. Metastasis is also angiogenesis-dependent—for a tumor cell to metastasize successfully, it generally must gain access to the vasculature in the primary tumor, survive the circulation, arrest in the microvasculature of the target organ, exit from this vasculature, grow in the target organ, and induce angiogenesis at the target site. Thus, angiogenesis appears to be necessary at the beginning as well as the completion of the metastatic cascade.

The criticality of angiogenesis to the growth and metastasis of neoplasms thus provides an optimal potential target for chemotherapeutic efforts. Appropriate anti-angiogenic agents may act directly or indirectly to influence tumor-associated angiogenesis either by delaying its onset (i.e., blocking an "angiogenic switch") or by blocking the sustained and focal neovascularization that is characteristic of many tumor types. Anti-angiogenesis therapies directed against the tumor-associated endothelium and the multiple molecular and cellular processes and targets implicated in sustained pathologic angiogenesis are being actively evaluated for their safety and efficacy in multiple clinical trials. See Deplanque & Harris, Anti-angiogenic Agents: Clinical Trial Design and Therapies in Development, EUR. J. CANCER, 36: 1713-1724 (2000). However, there has been limited success to date with the discovery and/or identification of safe and/or effective anti-angiogenic agents.

SUMMARY

The present disclosure relates generally to treating or preventing diseases associated with angiogenesis.

In one embodiment, there are provided methods for inhibiting angiogenesis with a compound of Formula (I)

Formula (I)

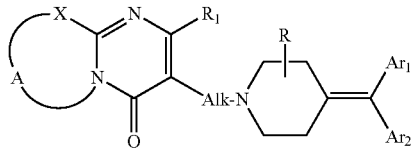

wherein:

R is hydrogen, hydroxy or lower alkyloxy;

$R_1$ is a member selected from the group consisting of hydrogen and lower alkyl;

Alk is a lower alkanediyl radical;

X is a member selected from the group consisting of —S—, —CH$_2$— and —C($R_2$)=C($R_3$)—, said $R_2$ and $R_3$ being each independently hydrogen or lower alkyl;

A is a bivalent radical having the formula —CH$_2$CH$_2$—, —CH$_2$CH$_2$CH$_2$— or

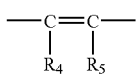

wherein $R_4$ and $R_5$ are each independently selected from the group consisting of hydrogen, halo, amino and lower alkyl; and $Ar_1$ and $Ar_2$ are each independently selected from the group consisting of pyridinyl, thienyl and phenyl, being optionally substituted with halo, hydroxy, lower alkyloxy, lower alkyl and trifluoromethyl; and pharmaceutically acceptable salts, solvates, and prodrugs thereof. Alternatively, Alk is an 1,2-ethanediyl radical.

In one embodiment, the compound of Formula (I) is Ritanserin.

In another embodiment, there are provided methods for inhibiting angiogenesis with a compound of Formula (II):

Formula (II)

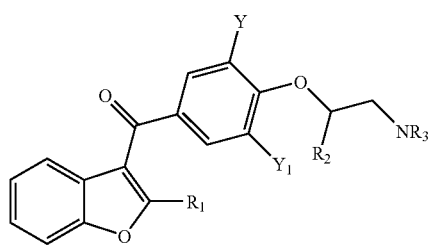

wherein:

$R_1$ is an alkyl group containing 1 to 6 carbon atoms;

$R_2$ is selected from the group consisting of hydrogen and methyl;

$NR_3$ is a radical selected from the group consisting of a dimethylamino, diethylamino, dipropylamino, piperidino, piperazino, pyrrolidino, morpholino, and N-substituted heteroaryl; and Y and $Y_1$ are independently selected from the group consisting of hydrogen, fluorine, bromine, chlorine, and iodine; and pharmaceutically acceptable salts, solvates, and prodrugs thereof. Alternatively, Y and $Y_1$ are identical and are selected from hydrogen, fluorine, bromine, chlorine, and iodine.

In one embodiment, the compound of Formula (II) is Amiodarone.

In another embodiment, there are provided methods for inhibiting angiogenesis with a compound of Formula (III):

Formula (III)

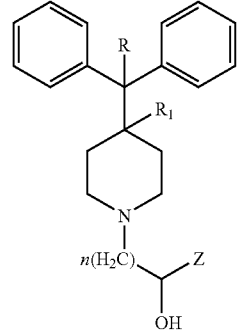

wherein

R is selected from the group consisting of hydrogen or hydroxy;

$R_1$ is hydrogen; or

R and $R_1$ taken together form a second bond between the carbon atoms bearing R and $R_1$;

n is a positive whole integer of from 1 to 3; and

Z is selected from the group consisting of thienyl, phenyl, or substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrrolidino, piperidino, morpholino, or N-(lower)alkylpiperazino; and pharmaceutically acceptable salts, solvates, and prodrugs thereof.

In one embodiment, the compound of Formula (III) is Terfenadine.

In another embodiment, there are provided methods for inhibiting angiogenesis with a compound of Formula (IV):

Formula (IV)

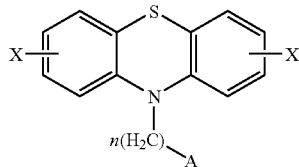

wherein

X at each occurrence independently represents hydrogen, chlorine or bromine;

A represents OH, OR, $NR_1R_2$, OC(O)R, OC(O)OR, C(O)OH, C(O)OR, C(O)$NR_1R_2$, OC(O)N $R_1R_2$, NHC(O)N $R_1R_2$ or NHC(NH)N $R_1R_2$;

R represents alkyl, cycloalkyl, heterocycle, aryl, arylalkyl, or heterocyclalkyl;

$R_1$ and $R_2$ each independently represent hydrogen, alkyl, cycloalkyl, heterocycle, aryl, arylalkyl, heterocyclalkyl, or $R_1$ and $R_2$ can together form a 3 to 8 membered heterocyclic ring which may be further optionally substituted with one to four $(CH_2)_nA$ substituents;

n is a number between 0 and 5 inclusive; and pharmaceutically acceptable salts, solvates, and prodrugs thereof.

In another embodiment, there are provided methods for inhibiting angiogenesis with a compound of Formula (IV-a):

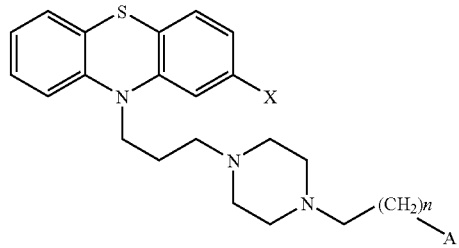

Formula (IV-a)

wherein

X represents hydrogen, chlorine or bromine;

A represents OH, OR, $NR_1R_2$, OC(O)R, OC(O)OR, C(O)OH, C(O)OR, C(O)$NR_1R_2$, OC(O)N $R_1R_2$, NHC(O)N $R_1R_2$ or NHC(NH)N $R_1R_2$;

R represents alkyl, cycloalkyl, heterocycle, aryl, arylalkyl, or heterocyclalkyl;

$R_1$ and $R_2$ each independently represent hydrogen, alkyl, cycloalkyl, heterocycle, aryl, arylalkyl, heterocyclalkyl, or $R_1$ and $R_2$ can together form a 3 to 8 membered heterocyclic ring;

n is a number between 0 and 5 inclusive; and pharmaceutically acceptable salts, solvates, and prodrugs thereof.

In one embodiment, the compound of Formula (IV) or Formula (IV-a) is Perphenazine.

In another embodiment, there are provided methods for inhibiting angiogenesis with a compound of Formula (V):

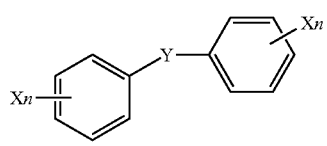

Formula (V)

wherein,

Y represents O, S, or S=O;

X at each occurrence independently represents halogen or OH; and n at each occurrence is independently an integer between 0 and 5 inclusive; and pharmaceutically acceptable salts, solvates, and prodrugs thereof.

Also provided are methods for inhibiting angiogenesis with a compound of Formula (V-a)

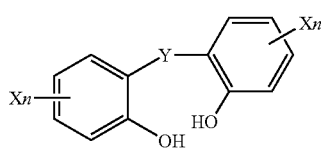

Formula (V-a)

wherein

Y represents O, S, or S=O;

X at each occurrence independently represents halogen or OH; and n at each occurrence is independently an integer between 0 and 5 inclusive; and pharmaceutically acceptable salts, solvates, and prodrugs thereof.

In one embodiment, the compound of Formula (V) or Formula (V-a) is Bithionol.

In another embodiment, there are provided methods for inhibiting angiogenesis with a compound of Formula (VI):

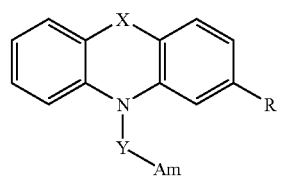

Formula (VI)

wherein

X represents a member selected from the group consisting of the ethylene radical —$CH_2CH_2$— and the vinylene radical —CH=CH—;

R represents a member selected from the group consisting of the methyl radical, the ethyl radical, the propyl radical, chlorine and bromine, Y represents an alkylene radical with 2-3 carbon atoms, and Am represents a member selected from the group consisting of a lower dialkylamino group, the pyrrolidinio, piperidino, piperazino, morpholino and N-methyl-piperidyl(2)-group; and pharmaceutically acceptable salts, solvates, and prodrugs thereof.

In one embodiment, the compound of Formula (VI) is Clomipramine.

Also provided are methods of inhibiting the growth or metastasis of an angiogenesis-dependent tumor with compounds of the present disclosure. Another embodiment is drawn to methods for treating a disease or disorder associated with angiogenesis such as neoplastic diseases, restenosis, rheumatoid arthritis, Crohn's disease, diabetic retinopathy, psoriasis, endometriosis, macular degeneration, neovascular glaucoma, and adiposity with compounds of the present disclosure.

DETAILED DESCRIPTION OF THE DISCLOSURE

Figure 1:
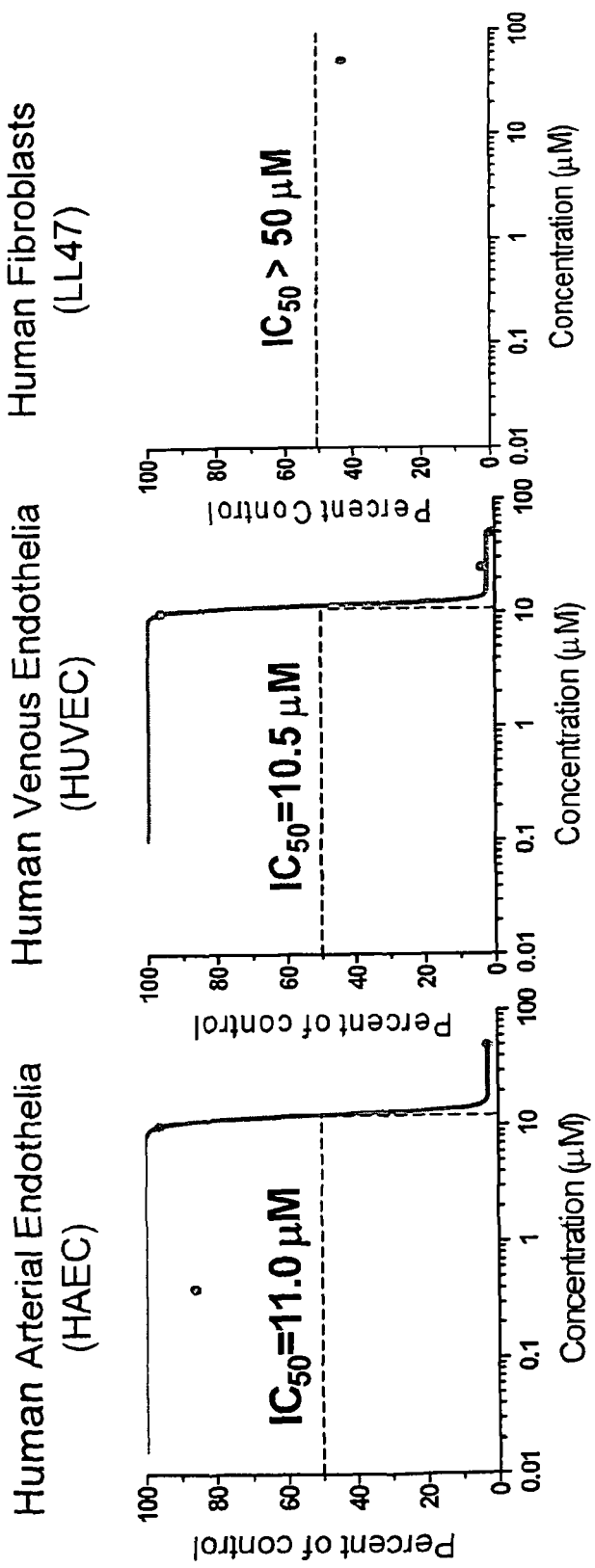
FIG. 1 shows the dose response curve plotted against concentration for cell proliferation assays using Ritanserin.
Figure 2:
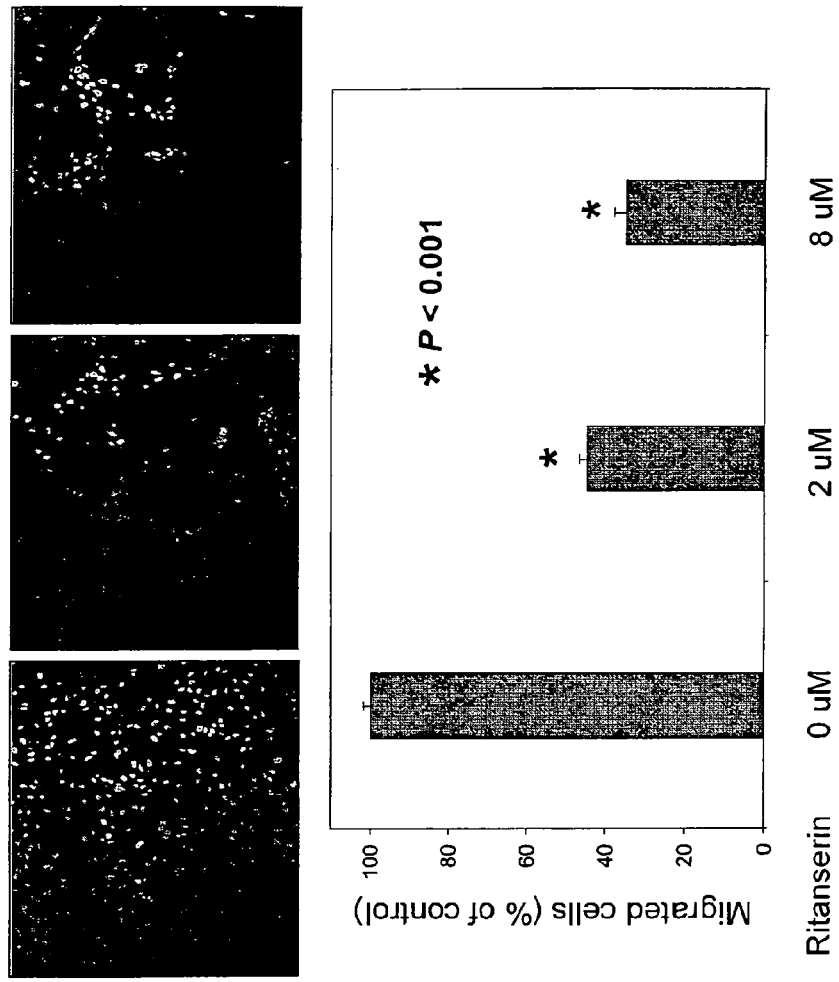
FIG. 2 shows the results of an endothelial cell migration assay using Ritanserin and plots the percent of migrated cells relative to a control.
Figure 3:
FIG. 3. shows the results of an endothelial tube-formation assay using Ritanserin and plots the percentage of tubule formation relative to a control.
Figure 3:
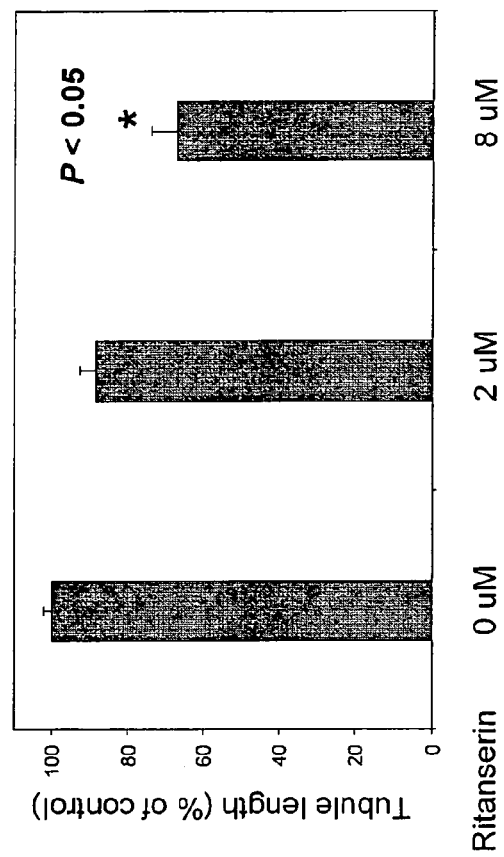
Figure 4:
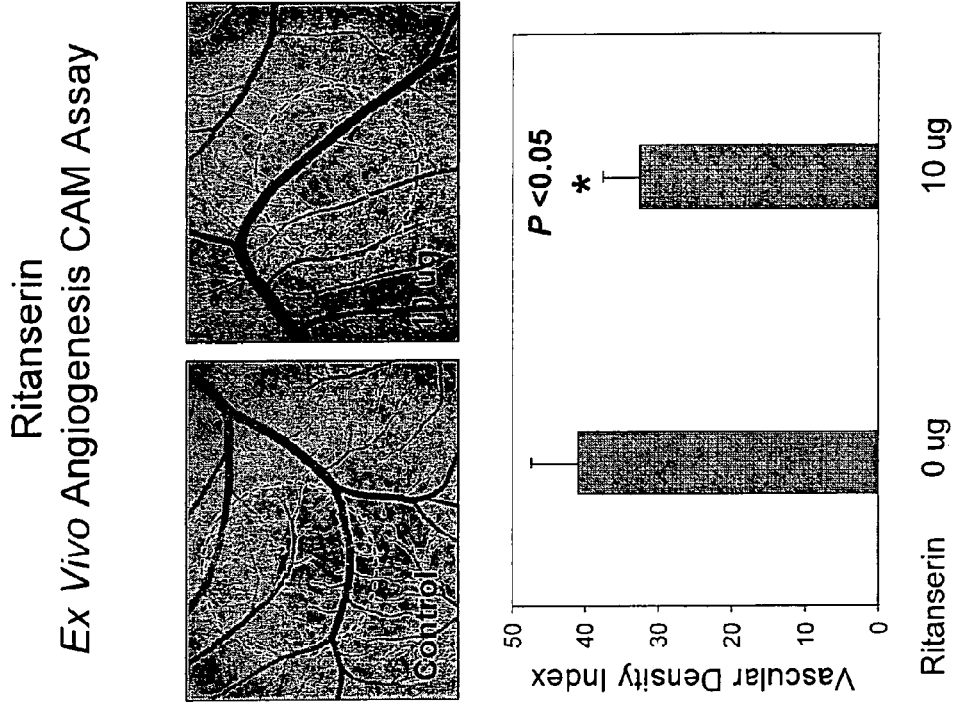
FIG. 4 shows the results of an ex vivo angiogenesis CAM assay using Ritanserin and plots the vascular density index.
Figure 5:
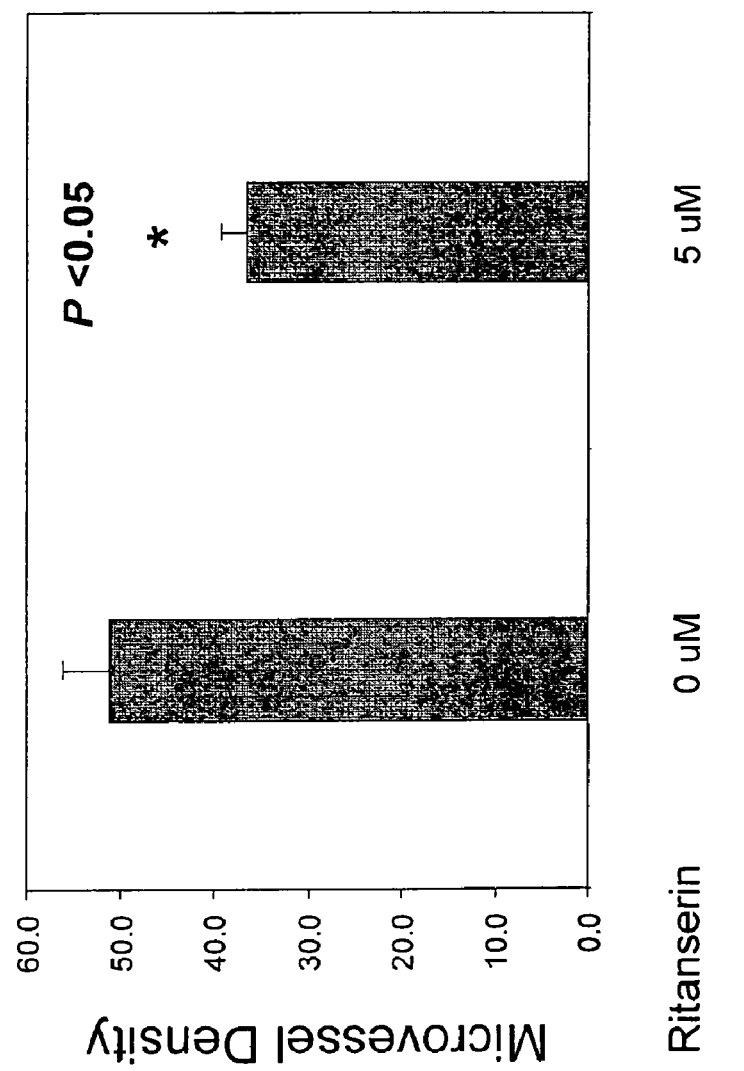
FIG. 5. plots the results in microvessel density of an in vivo mouse matrigel plug assay using Ritanserin.
Figure 6:
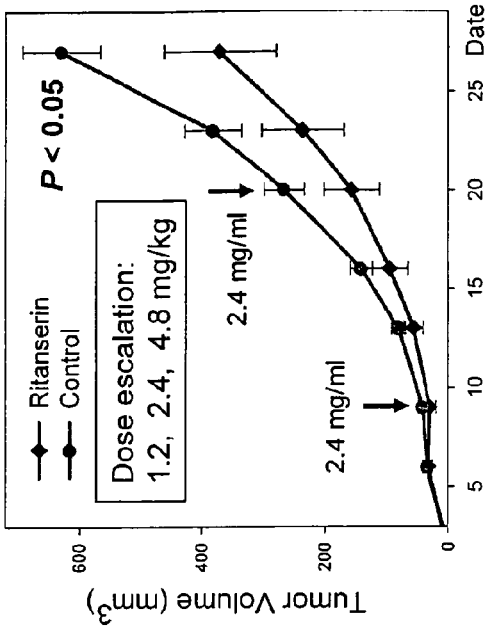
FIG. 6 shows the results of a xenograft mouse model assay using Ritanserin and plots the change in tumor volume over time.
Figure 6:
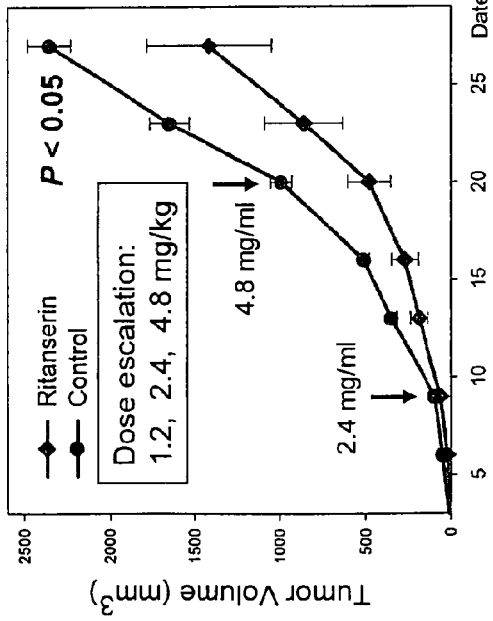
Figure 7:
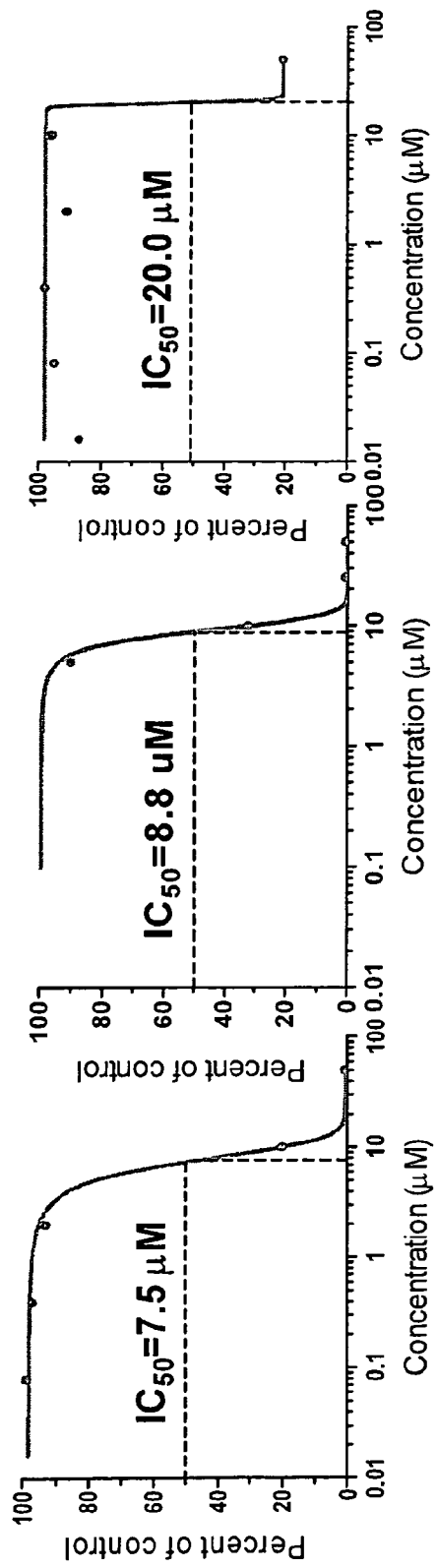
FIG. 7 shows the dose response curve plotted against concentration for cell proliferation assays using Amiodarone Hydrochloride.
Figure 8:
FIG. 8 shows the results of an endothelial cell migration assay using Amiodarone Hydrochloride and plots the percent of migrated cells relative to a control.
Figure 8:
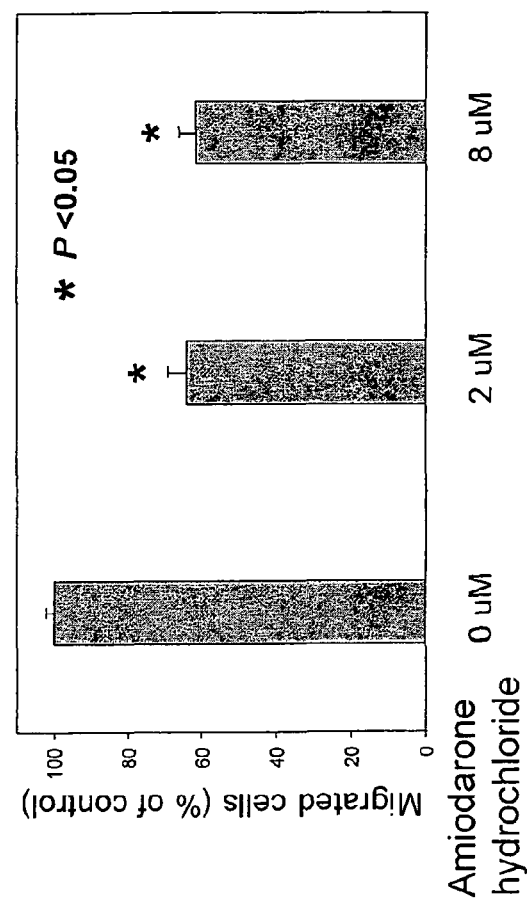
Figure 9:
FIG. 9 shows the results of an endothelial tube-formation assay using Amiodarone Hydrochloride and plots the percentage of tubule formation relative to a control.
Figure 9:
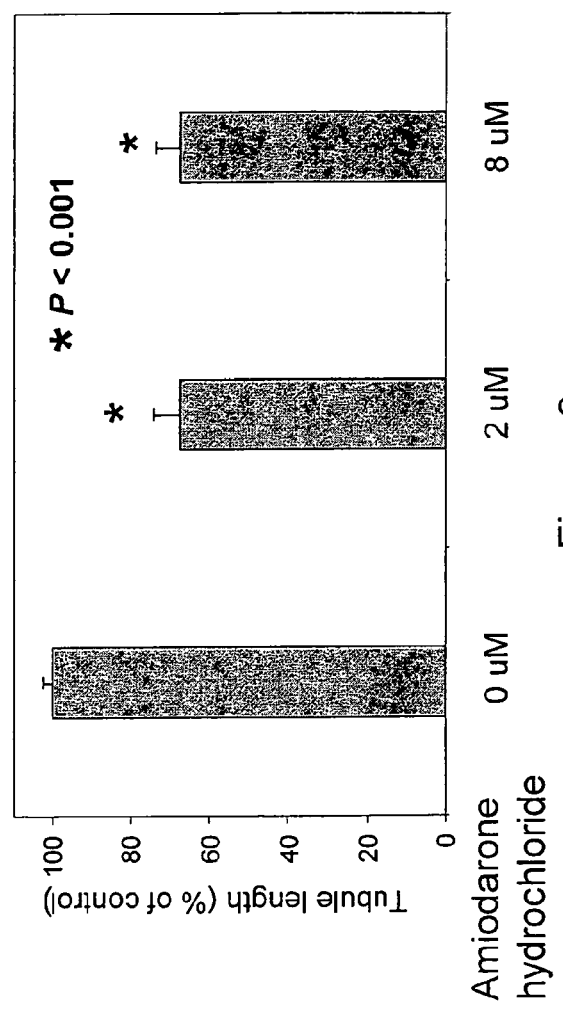
Figure 10:
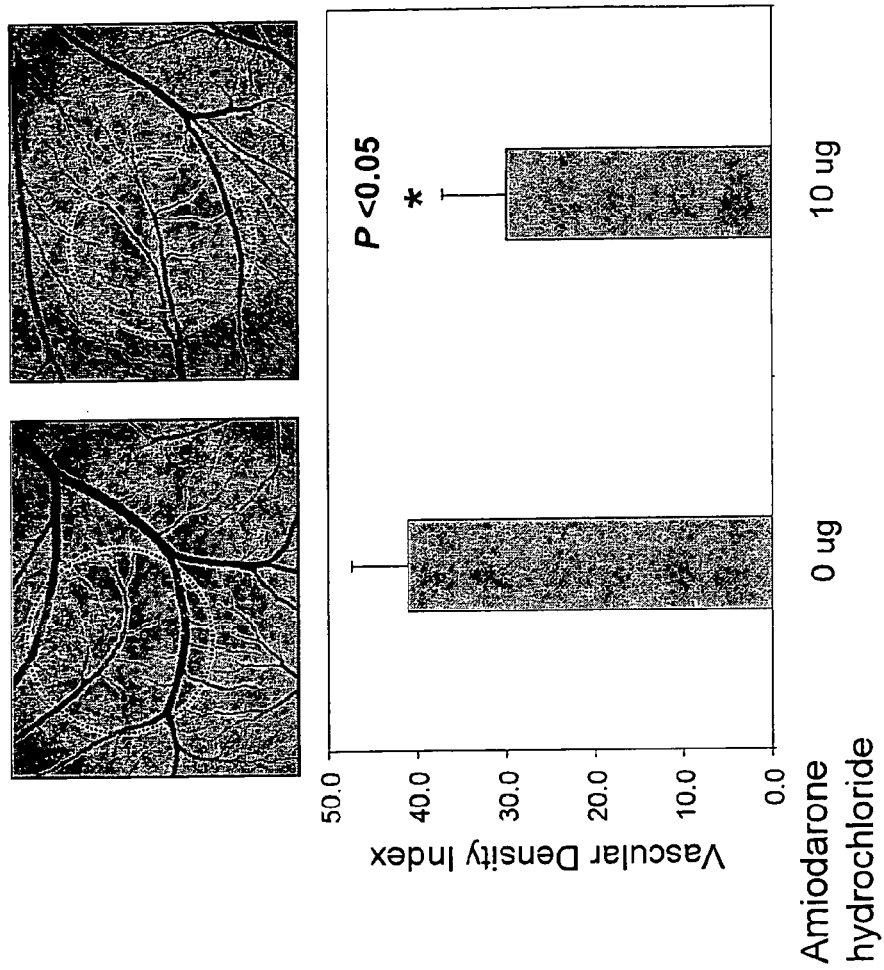
FIG. 10 shows the results of an ex vivo angiogenesis CAM assay using Amiodarone and plots the vascular density index.
Figure 11:
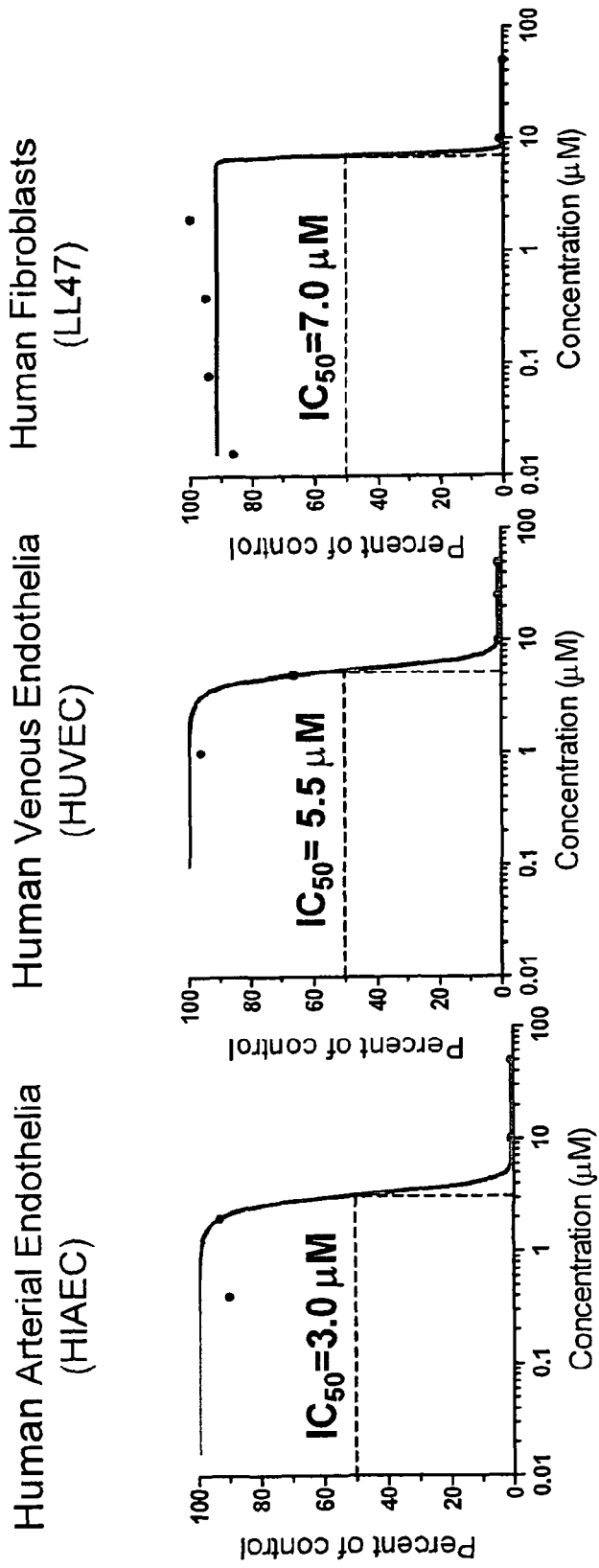
FIG. 11 shows the dose response curve plotted against concentration for cell proliferation assays using Terfenadine.
Figure 12:
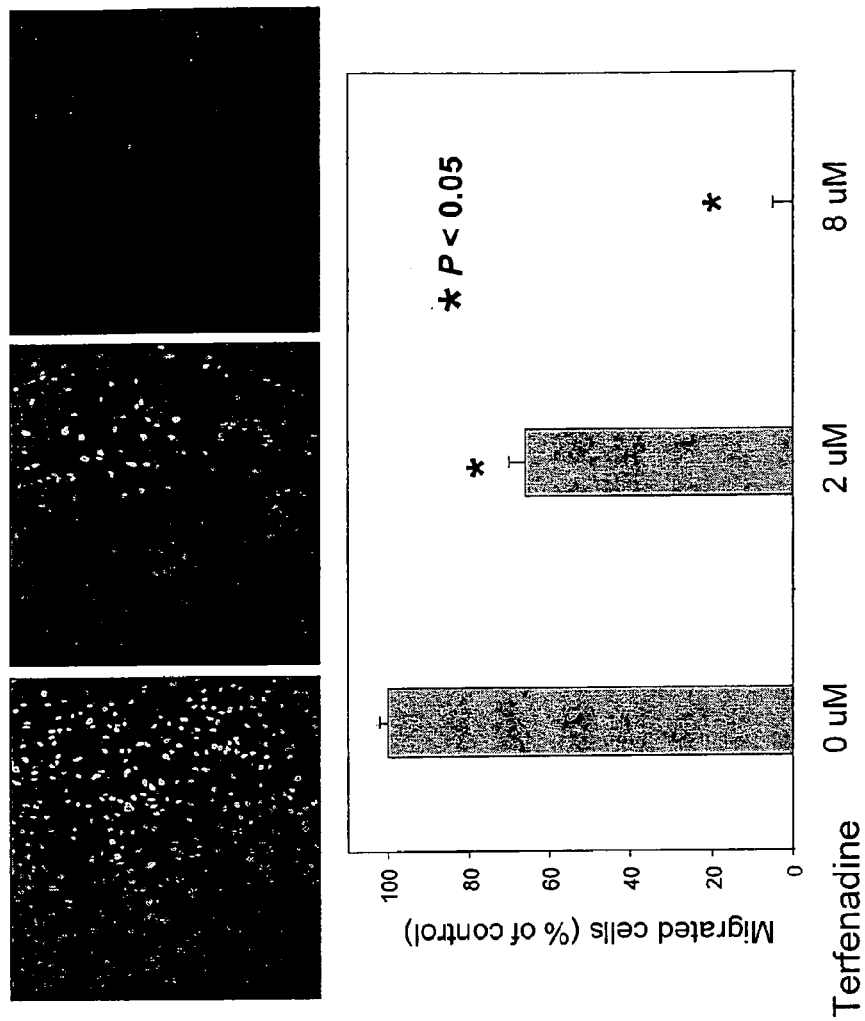
FIG. 12 shows the results of an endothelial cell migration assay using Terfenadine and plots the percent of migrated cells relative to a control.
Figure 13:
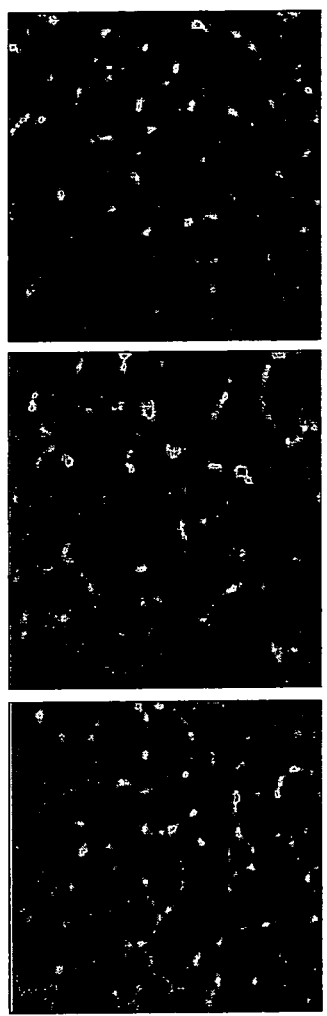
FIG. 13 shows the results of an endothelial tube-formation assay using Terfenadine and plots the percentage of tubule formation relative to a control.
Figure 13:
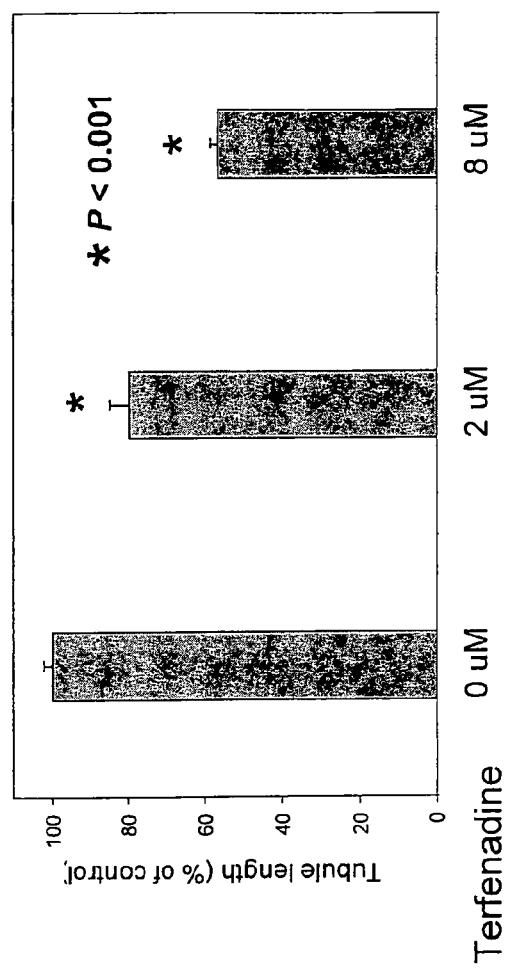
Figure 14:
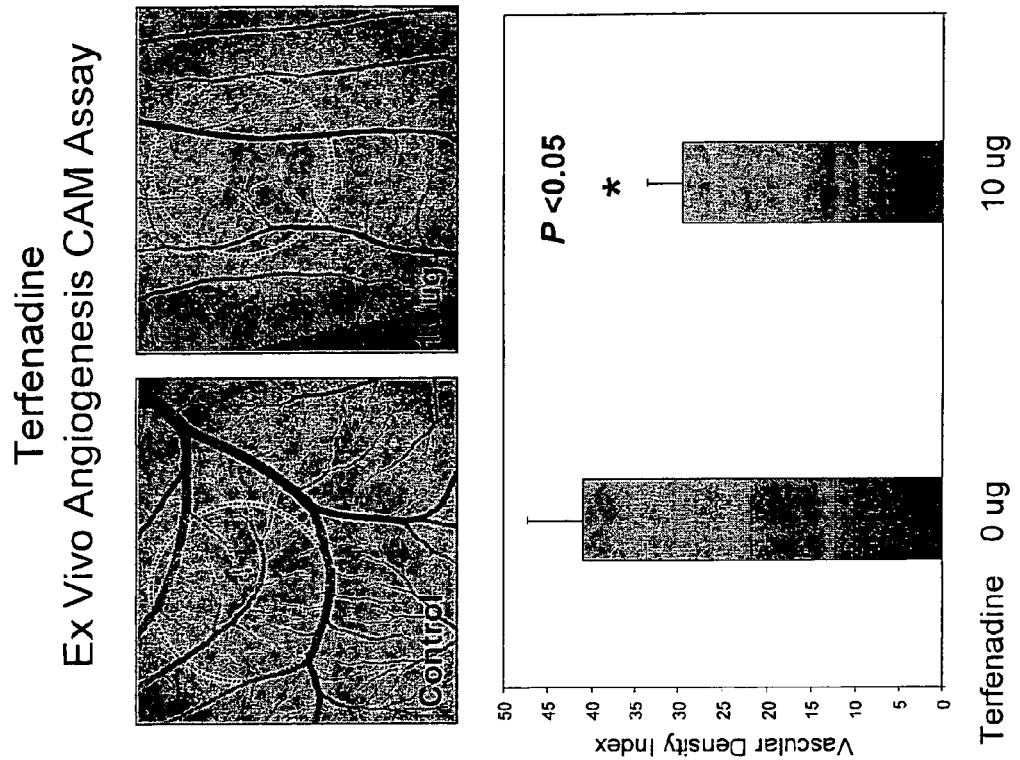
FIG. 14. shows the results of an ex vivo angiogenesis CAM assay using Terfenadine and plots the vascular density index.
Figure 15:
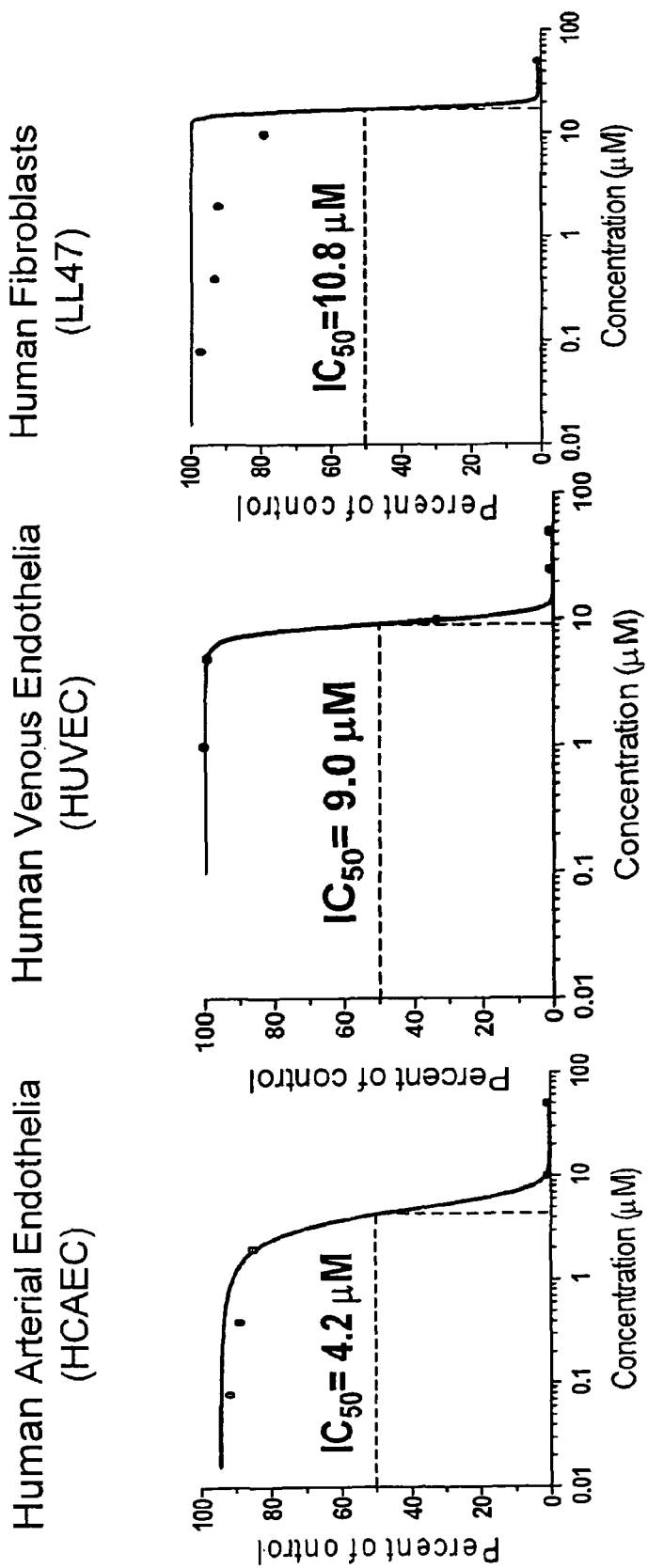
FIG. 15 shows the dose response curve plotted against concentration for cell proliferation assays using Perphenazine.
Figure 16:
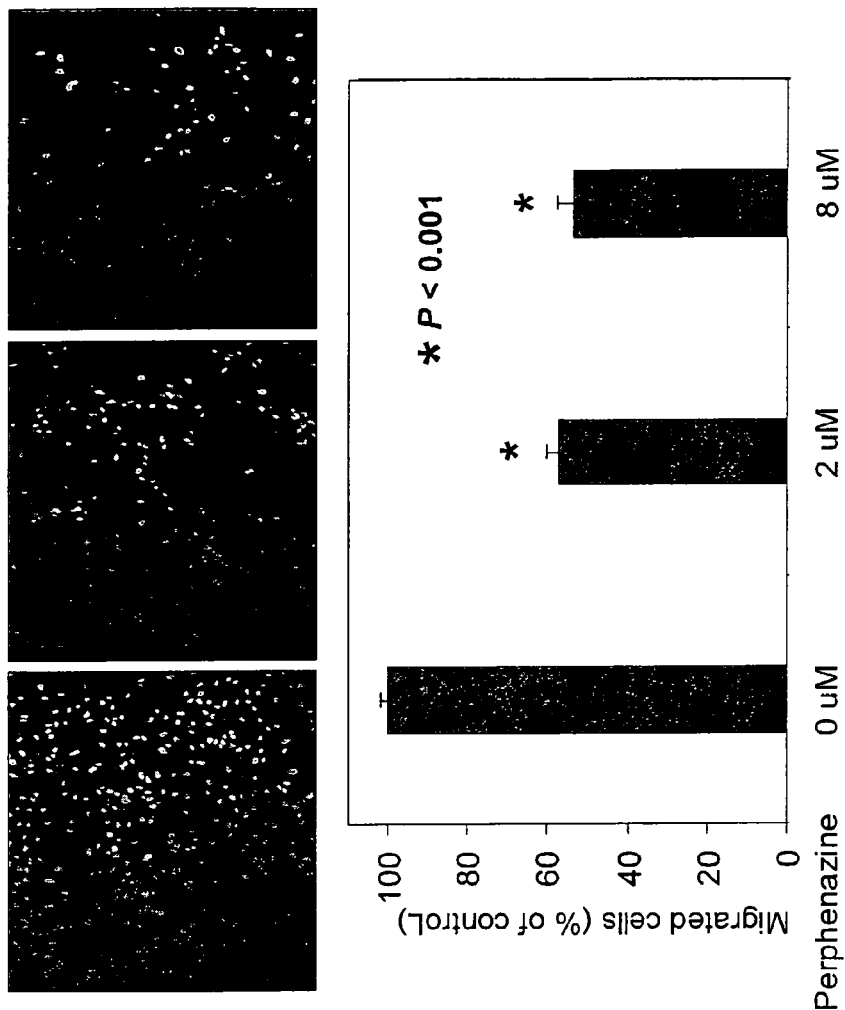
FIG. 16 shows the results of an endothelial cell migration assay using Perphenazine and plots the percent of migrated cells relative to a control.
Figure 17:
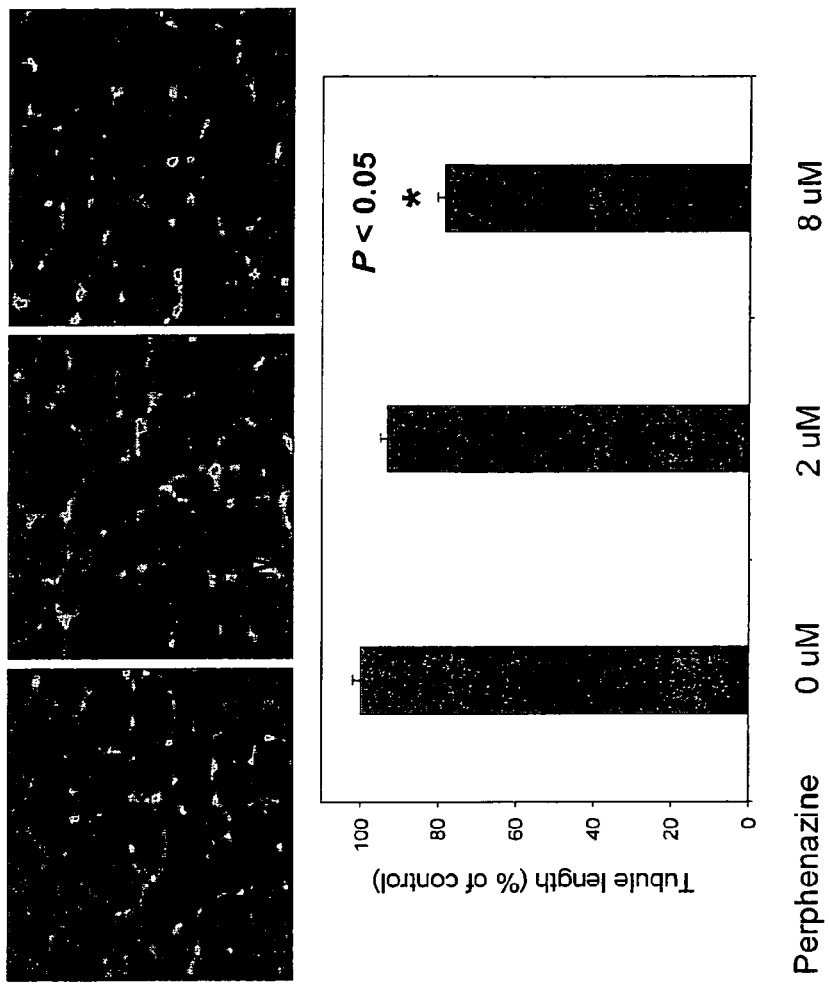
FIG. 17 shows the results of an endothelial tube-formation assay using Perphenazine and plots the percentage of tubule formation relative to a control.
Figure 18:
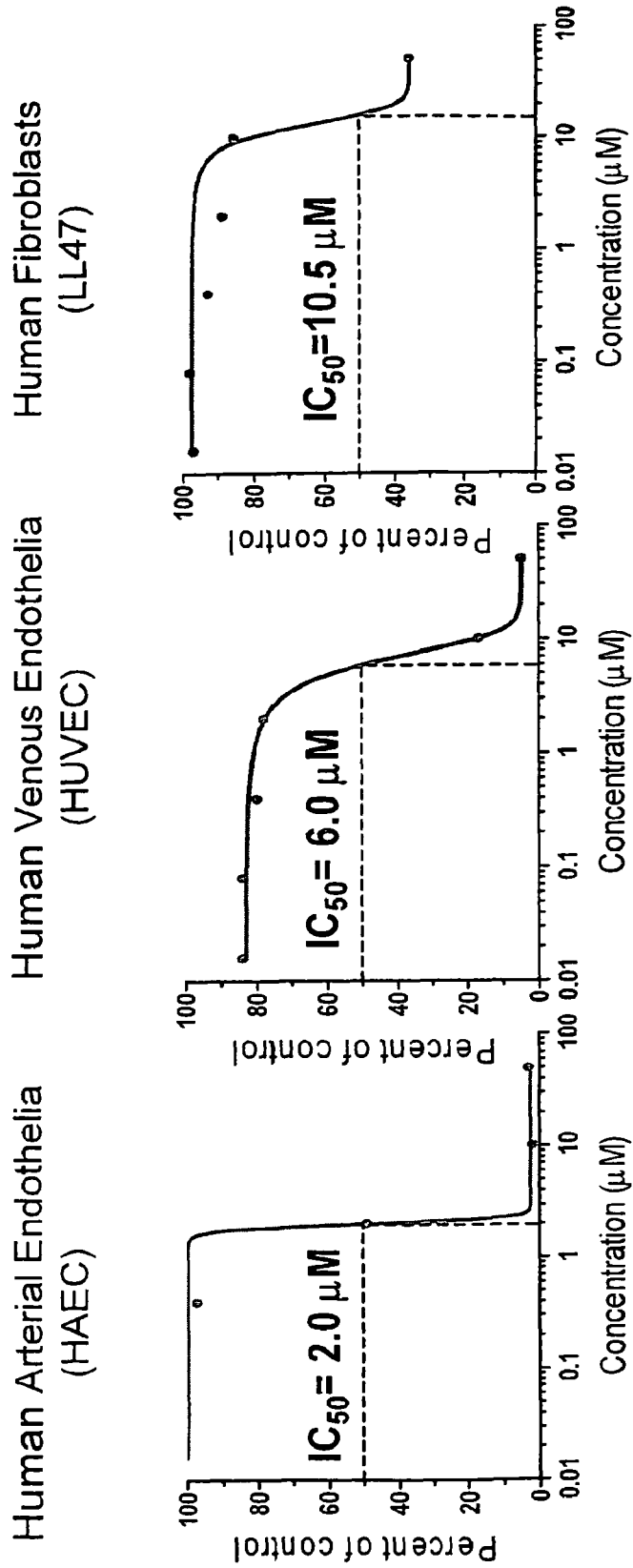
FIG. 18 shows the dose response curve plotted against concentration for cell proliferation assays using Bithionol.
Figure 19:
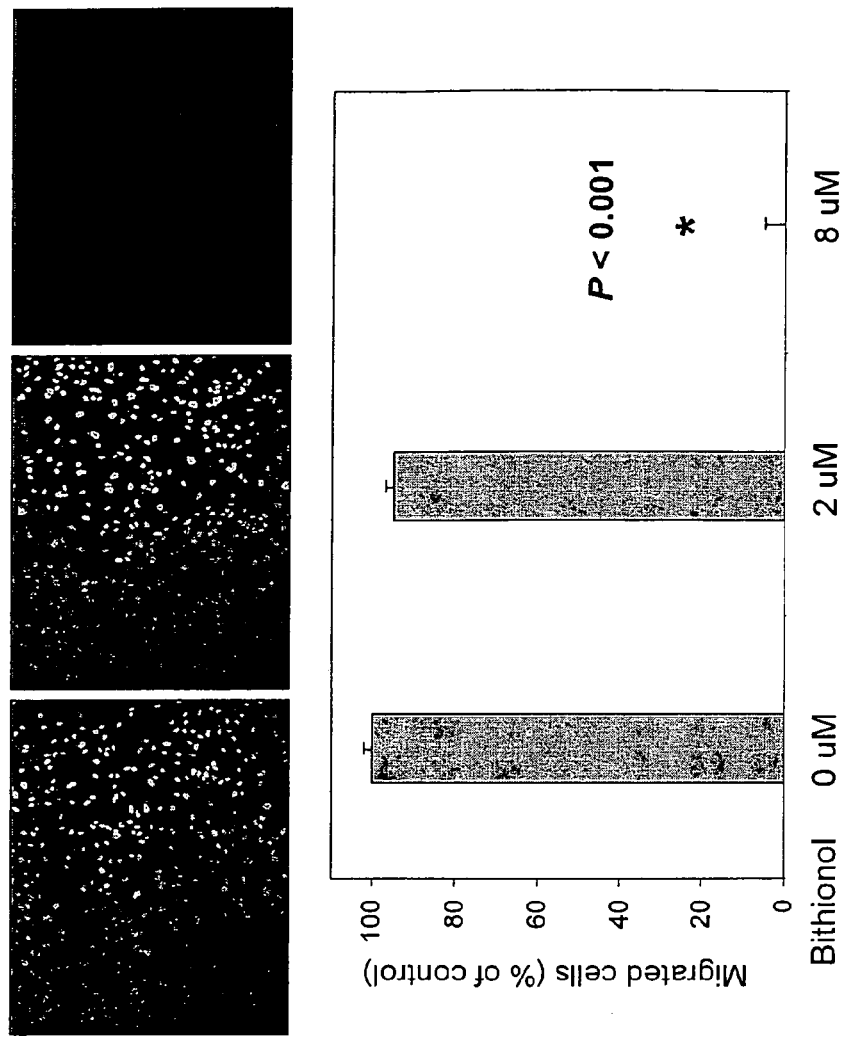
FIG. 19 shows the results of an endothelial cell migration assay using Bithionol and plots the percent of migrated cells relative to a control.
Figure 20:
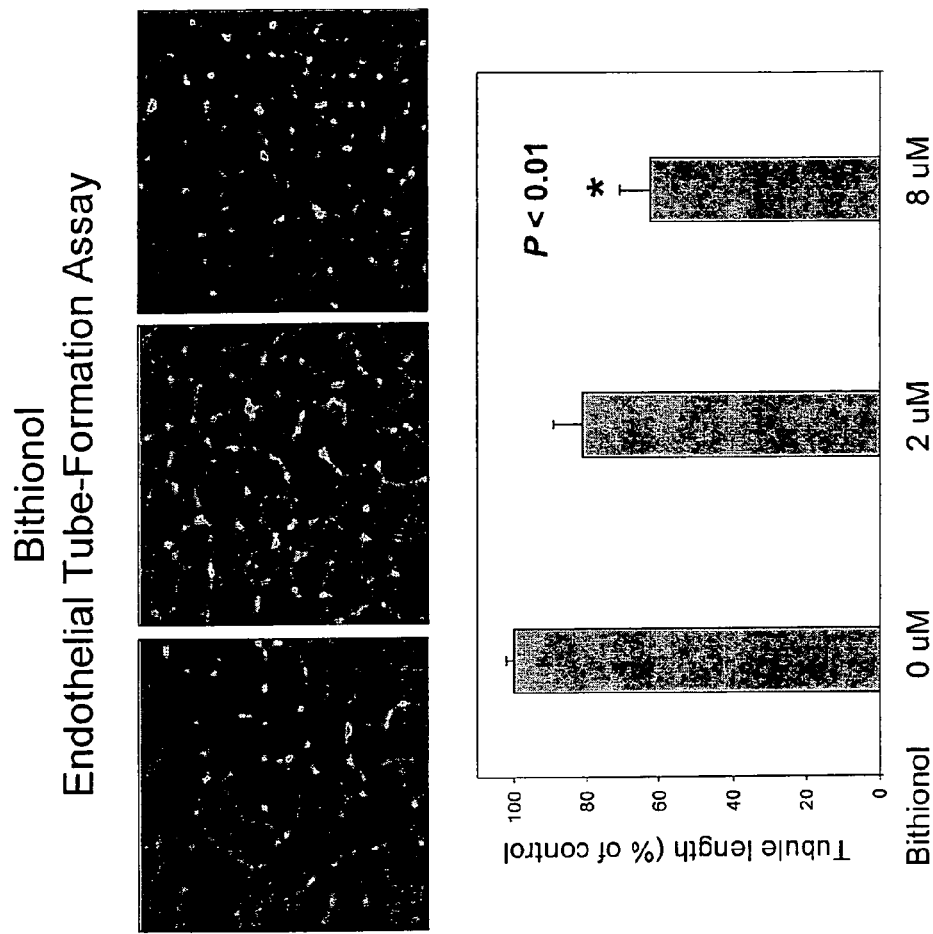
FIG. 20 shows the results of an endothelial tube-formation assay using Bithionol and plots the percentage of tubule formation relative to a control.
Figure 21:
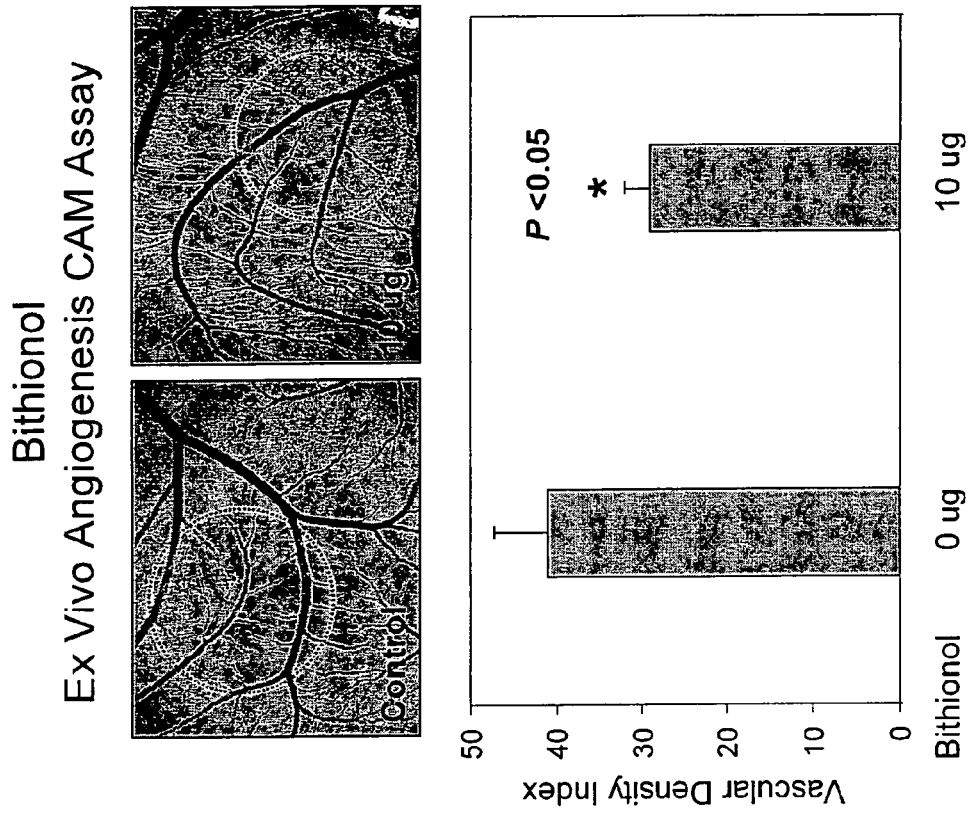
FIG. 21. shows the results of an ex vivo angiogenesis CAM assay using Bithionol and plots the vascular density index.
Figure 22:
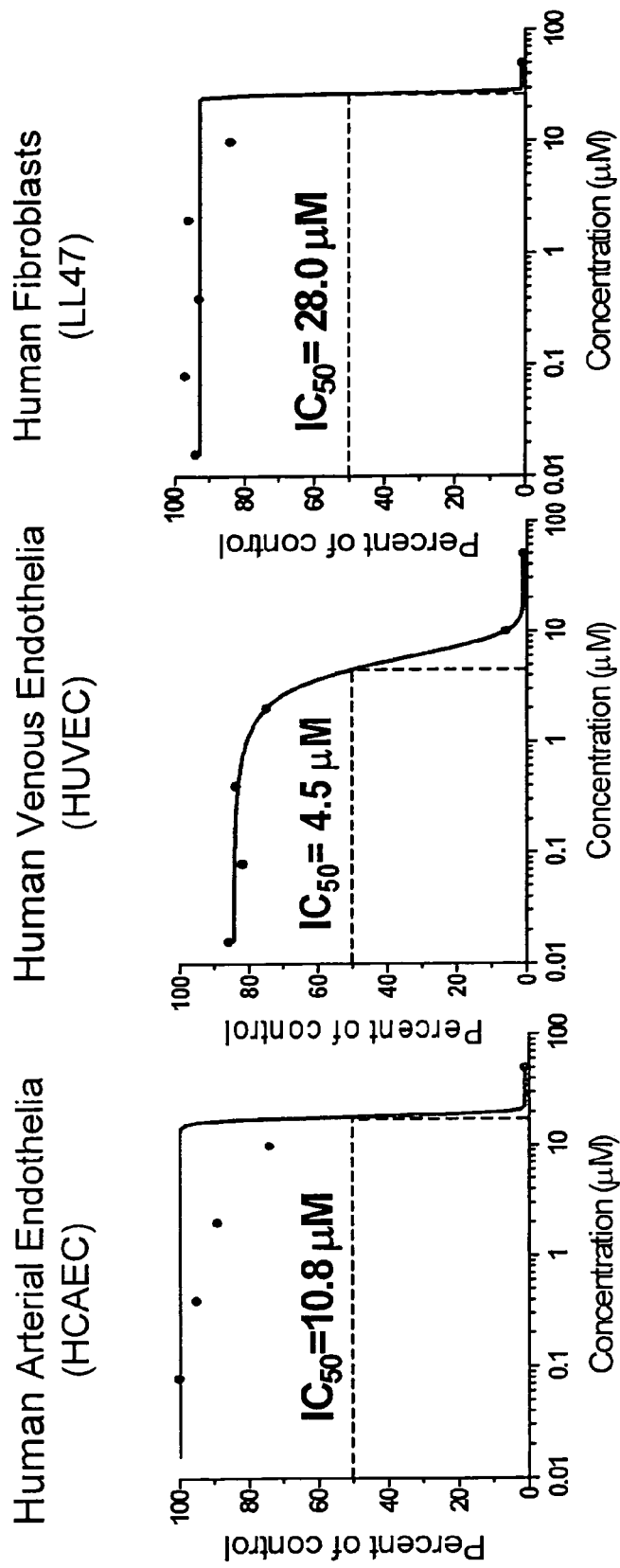
FIG. 22 shows the dose response curve plotted against concentration for cell proliferation assays using Clomipramine.
Figure 23:
FIG. 23 shows the results of an endothelial cell migration assay using Clomipramine and plots the percent of migrated cells relative to a control.
Figure 23:
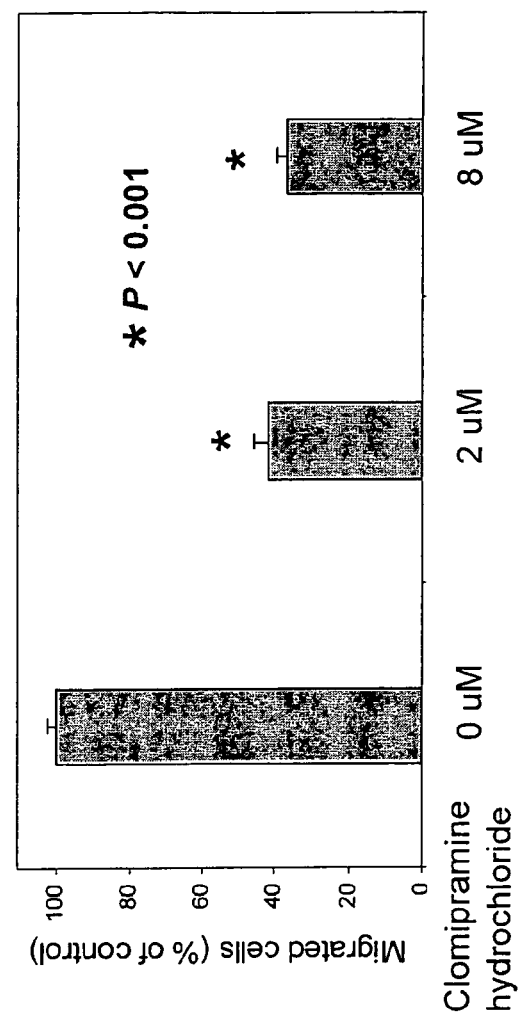
Figure 24:
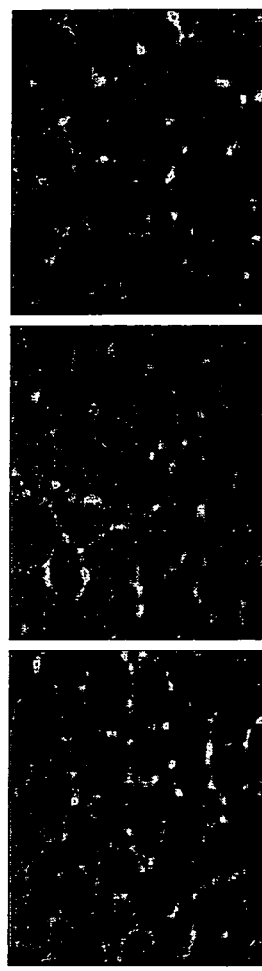
FIG. 24 shows the results of an endothelial tube-formation assay using Clomipramine and plots the percentage of tubule formation relative to a control.
Figure 24:
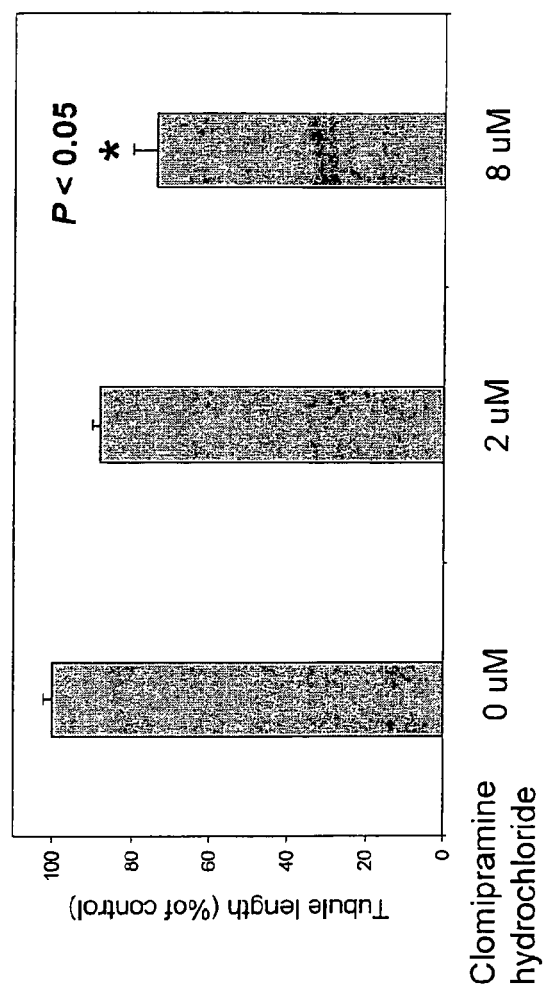
Figure 25:
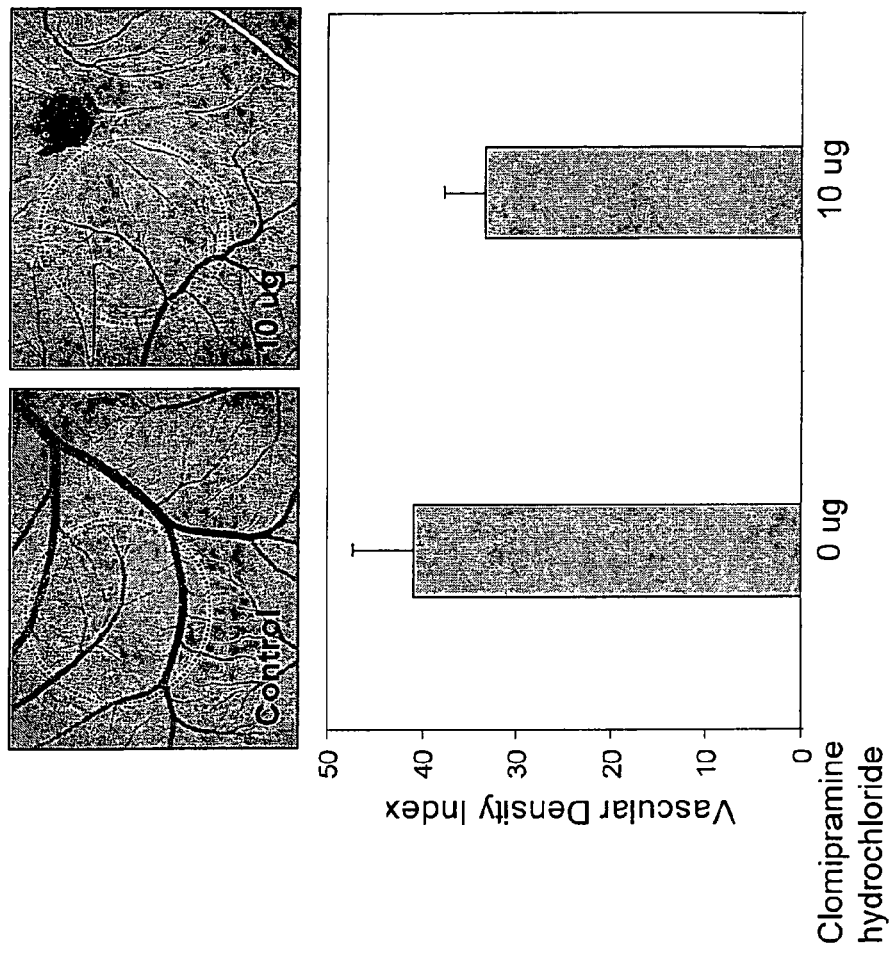
FIG. 25. shows the results of an ex vivo angiogenesis CAM assay using Clomipramine and plots the vascular density index.

The present disclosure relates generally to treating or preventing diseases associated with angiogenesis in a patient in need thereof by administering to the patient certain compounds found to inhibit or substantially reduce angiogenesis.

As employed above and throughout the disclosure, the following terms, unless otherwise indicated, shall be understood to have the following meanings.

"Alkyl" refers to an aliphatic hydrocarbon group which may be straight, branched or cyclic having from 1 to about 10 carbon atoms in the chain, and all combinations and subcombinations of ranges therein. "Branched" refers to an alkyl group in which a lower alkyl group, such as methyl, ethyl or propyl, is attached to a linear alkyl chain. In certain embodiments, the alkyl group is a $C_1$-$C_4$ alkyl group, i.e., a branched or linear alkyl group having from 1 to about 4 carbons. In other embodiments, the alkyl group is a $C_1$-$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl and decyl.

"Aryl" refers to an aromatic carbocyclic radical containing from about 6 to about 10 carbons, and all combinations and subcombinations of ranges therein. The aryl group may be optionally substituted with one or two or more substituents. Exemplary aryl groups include monocyclic groups, such as phenyl, and bicyclic groups, such as naphthyl.

"Heteroaryl" refers to an aromatic carbocyclic radical containing from about 4 to about 10 members, and all combinations and subcombinations of ranges therein, wherein one or more of the members is an element other than carbon, for example, nitrogen, oxygen or sulfur.

Exemplary heteroaryl groups include monocylic groups, such as pyridyl, and bicyclic groups, such as indolyl.

"Arylalkyl" refers to an alkyl substituted with an aryl group. A "$C_1$-$C_4$ arylalkyl group", for example, has a $C_1$-$C_4$ alkyl group substituted with an aryl group.

"Heteroarylalkyl" refers to an alkyl substituted with a heteroaryl group. A "$C_1$-$C_4$ heteroarylalkyl group", for example, has a $C_1$-$C_4$ alkyl group substituted with an heteroaryl group.

The term "cycloalkyl" used alone or as part of a larger moiety shall include cyclic $C_3$-$C_{10}$ hydrocarbons which are completely saturated or which contain one or more units of unsaturation, but which are not aromatic. Cycloaliphatic groups are typically $C_3$-$C_{10}$, more typically $C_3$-$C_7$.

The term "non-aromatic heterocycle", used alone or as part of a larger moiety as in "heterocyclalkyl", refers to non-aromatic ring systems typically having five to fourteen members, preferably five to ten, in which one or more ring carbons, preferably one to four, are each replaced by a heteroatom such as N, O, or S.

"Effective amount" refers to an amount of a compound as described herein that may be therapeutically effective to treat a disease or disorder associated with angiogenesis. The precise amount of these compounds required will vary with the particular compounds or employed, the age and condition of the subject to be treated, and the nature and severity of the condition. However, the effective amount may be determined by one of ordinary skill in the art with only routine experimentation.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Patient" refers to animals, including mammals, preferably humans.

"Metabolite" refers to any substance resulting from chemical changes involved in the processes of growth and repair in a living organism, including the anabolic and catabolic processes.

A "Prodrug" is a compound that is converted within the body into its active form that has a medical effect. Prodrugs may be useful when the active drug may be too toxic to administer systemically, the active drug is absorbed poorly by the digestive tract, or the body breaks down the active drug before it reaches its target. Methods of making prodrugs are disclosed in Hans Bundgaard, DESIGN OF PRODRUGS (Elsevier Science Publishers B.V. 1985), which is incorporated herein by reference in its entirety.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "comprising" (and its grammatical variations) as used herein is used in the inclusive sense of "having" or "including" and not in the exclusive sense of "consisting only of." The term "consisting essentially of" as used herein is intended to refer to including that which is explicitly recited along with what does not materially affect the basic and novel characteristics of that recited or specified.

The terms "a", "an", and "the" as used herein are understood to encompass the plural as well as the singular unless the context clearly dictates otherwise.

Certain acidic or basic compounds of the present disclosure may exist as zwitterions. All forms of the compounds, including free acid, free base and zwitterions, are contemplated to be within the scope of the present disclosure.

In the formulas described and claimed herein, it is intended that when any symbol appears more than once in a particular formula or substituent, its meaning in each instance is independent of the other.

In one embodiment, there are provided methods for inhibiting angiogenesis with a compound of Formula (I)

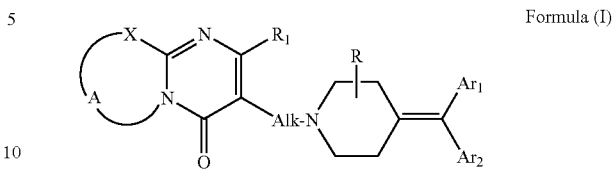

Formula (I)

wherein:

R is hydrogen, hydroxy or lower alkyloxy;

$R_1$ is a member selected from the group consisting of hydrogen and lower alkyl; Alk is a lower alkanediyl radical;

X is a member selected from the group consisting of —S—, —$CH_2$— and —$C(R_2)$=$C(R_3)$—, said $R_2$ and $R_3$ being each independently hydrogen or lower alkyl;

A is a bivalent radical having the formula —$CH_2CH_2$—, —$CH_2CH_2CH_2$— or

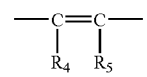

wherein $R_4$ and $R_5$ are each independently selected from the group consisting of hydrogen, halo, amino and lower alkyl; and $Ar_1$ and $Ar_2$ are each independently selected from the group consisting of pyridinyl, thienyl and phenyl, being optionally substituted with halo, hydroxy, lower alkyloxy, lower alkyl and trifluoromethyl; and pharmaceutically acceptable salts, solvates, and prodrugs thereof. Alternatively, Alk is an 1,2-ethanediyl radical.

In one embodiment, the compound of Formula (I) is Ritanserin.

Methods of synthesizing compounds of Formula (I) are well known in the art and disclosed in U.S. Pat. No. 4,533,665 to Kennis et al. and U.S. Pat. No. 4,485,107 to Kennis et al., both of which are incorporated herein by reference in their entireties.

In another embodiment, there are provided methods for inhibiting angiogenesis with a compound of Formula (II):

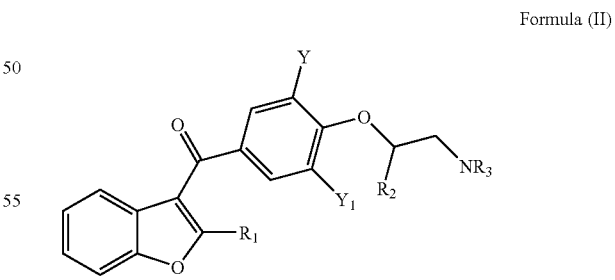

Formula (II)

wherein:

$R_1$ is an alkyl group containing 1 to 6 carbon atoms;

$R_2$ is selected from the group consisting of hydrogen and methyl;

$NR_3$ is a radical selected from the group consisting of a dimethylamino, diethylamino, dipropylamino, piperidino, piperazino, pyrrolidino, morpholino, and N-substituted heteroaryl; and Y and $Y_1$ are independently selected from the group consisting of hydrogen, fluorine, bromine, chlorine, and iodine; and pharmaceutically acceptable salts, solvates, and prodrugs thereof. Alternatively, Y and $Y_1$ are identical and are selected from hydrogen, fluorine, bromine, chlorine, and iodine.

In certain embodiments, $NR_3$ is selected from the group consisting of dimethylamino, diethylamino, dipropylamino, piperidino, pyrrolidino, and morpholino; Y and $Y_1$ are the same or different and are selected from the group consisting of hydrogen, iodine, and bromine.

In one embodiment, the compound of Formula (II) is Amiodarone.

Methods of synthesizing compounds of Formula (II) are well known in the art and are disclosed in U.S. Pat. No. 3,248,401 to Tondeur et al. and is incorporated herein by reference in its entirety.

In another embodiment, there are provided methods for inhibiting angiogenesis with a compound of Formula (III):

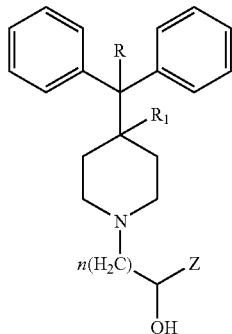

Formula (III)

wherein

R is selected from the group consisting of hydrogen or hydroxy;

$R_1$ is hydrogen; or

R and $R_1$ taken together form a second bond between the carbon atoms bearing R and $R_1$;

n is an integer from 1 to 3; and

Z is selected from the group consisting of thienyl, phenyl, or substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrrolidino, piperidino, morpholino, or N-(lower)alkylpiperazino; and pharmaceutically acceptable salts, solvates, and prodrugs thereof.

In one embodiment, the compound of Formula (III) is Terfenadine.

Methods of synthesizing compounds of Formula (III) are well known in the art and disclosed in U.S. Pat. No. 3,878,217 to Carr et al. and U.S. Pat. No. 4,254,129 to Carr et al., both of which are incorporated herein by reference in their entireties.

In another embodiment, there are provided methods for inhibiting angiogenesis with a compound of Formula (IV):

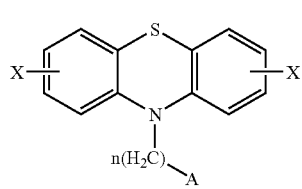

Formula (IV)

wherein

X at each occurrence independently represents hydrogen, chlorine or bromine;

A represents OH, OR, $NR_1R_2$, OC(O)R, OC(O)OR, C(O)OH, C(O)OR, C(O)$NR_1R_2$, OC(O)N $R_1R_2$, NHC(O)N $R_1R_2$ or NHC(NH)N $R_1R_2$;

R represents alkyl, cycloalkyl, heterocycle, aryl, arylalkyl, or heterocyclalkyl;

$R_1$ and $R_2$ each independently represent hydrogen, alkyl, cycloalkyl, heterocycle, aryl, arylalkyl, heterocyclalkyl, or $R_1$ and $R_2$ can together form a 3 to 8 membered heterocyclic ring which may be further optionally substituted with one to four $(CH_2)_n$A substituents;

n is a number between 0 and 5 inclusive; and pharmaceutically acceptable salts, solvates, and prodrugs thereof.

Methods of synthesizing compounds of Formula (IV) are well known in the art and are disclosed in U.S. Pat. No. 2,645,640 to Choisy-le-Roi and is incorporated herein by reference in its entirety.

In another embodiment, there are provided methods for inhibiting angiogenesis with a compound of Formula (IV-a):

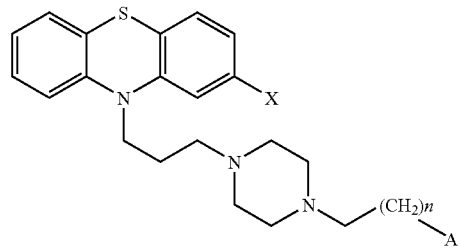

Formula (IV-a)

wherein

X represents hydrogen, chlorine or bromine;

A represents OH, OR, $NR_1R_2$, OC(O)R, OC(O)OR, C(O)OH, C(O)OR, C(O)$NR_1R_2$, OC(O)N $R_1R_2$, NHC(O)N $R_1R_2$ or NHC(NH)N $R_1R_2$;

R represents alkyl, cycloalkyl, heterocycle, aryl, arylalkyl, or heterocyclalkyl;

$R_1$ and $R_2$ each independently represent hydrogen, alkyl, cycloalkyl, heterocycle, aryl, arylalkyl, heterocyclalkyl, or $R_1$ and $R_2$ can together form a 3 to 8 membered heterocyclic ring;

n is a number between 0 and 5 inclusive; and pharmaceutically acceptable salts, solvates, and prodrugs thereof.

In one embodiment, the compound of Formula (IV) or Formula (IV-a) is Perphenazine.

Methods of synthesizing compounds of Formula (IV-a) are well known in the art and are disclosed in U.S. Pat. No. 2,860,138 to Sherlock et al. and is incorporated herein by reference in its entirety.

In another embodiment, there are provided methods for inhibiting angiogenesis with a compound of Formula (V):

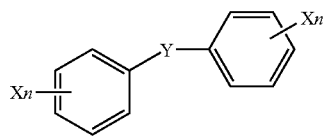
Formula (V)

wherein,

Y represents O, S, or S=O;

X at each occurrence independently represents halogen or OH; and n is an integer between 0 and 5 inclusive; and pharmaceutically acceptable salts, solvates, and prodrugs thereof.

In one embodiment, the compound of Formula (V) or Formula (V-a) is Bithionol.

Also provided are methods for inhibiting angiogenesis with a compound of Formula (V-a)

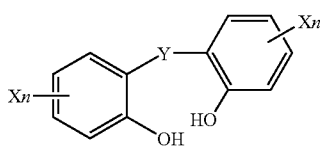
Formula (V-a)

wherein

Y represents O, S, or S=O;

X at each occurrence independently represents halogen or OH; and n at each occurrence is independently an integer between 0 and 5 inclusive; and pharmaceutically acceptable salts, solvates, and prodrugs thereof.

Methods of synthesizing compounds of Formula (V) and Formula (V-a) are well known in the art and disclosed in U.S. Pat. No. 3,506,720 to Basel et al. and U.S. Pat. No. 2,849,494 to Cooper et al., and are both incorporated herein by reference in their entireties.

In another embodiment, there are provided methods for inhibiting angiogenesis with a compound of Formula (VI):

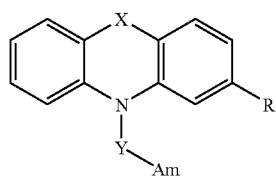
Formula (VI)

wherein

X represents a member selected from the group consisting of the ethylene radical —CH$_2$CH$_2$— and the vinylene radical —CH=CH—;

R represents a member selected from the group consisting of the methyl radical, the ethyl radical, the propyl radical, chlorine and bromine, Y represents an alkylene radical with 2-3 carbon atoms, and Am represents a member selected from the group consisting of a lower dialkylamino group, the pyrrolidinio, piperidino, piperazino, morpholino and N-methyl-piperidyl(2)-group; and pharmaceutically acceptable salts, solvates, and prodrugs thereof.

In one embodiment, the compound of Formula (VI) is Clomipramine.

Methods of synthesizing compounds of Formula (VI) are well known in the art and disclosed in U.S. Pat. No. 3,467,650 to Riehen et al. and is incorporated herein by reference in its entirety.

In another embodiment, there are provided methods for inhibiting angiogenesis with a compound selected from Ritanserin, Amiodarone hydrochloride, Terfenadine, Perphenazine, Bithionol, Bithionol sulfoxide, Clomipramine hydrochloride, Fexofenadine, and combinations thereof.

Also provided are methods of inhibiting the growth or metastasis of an angiogenesis-dependent tumor with compounds of the present disclosure. Another embodiment is drawn to methods for treating a disease or disorder associated with angiogenesis such as neoplastic diseases, restenosis, rheumatoid arthritis, Crohn's disease, diabetic retinopathy, psoriasis, endometriosis, macular degeneration, neovascular glaucoma, and adiposity with compounds of the present disclosure.

In certain embodiments, the present disclosure is directed to methods for inhibiting angiogenesis and/or inhibiting the growth or metastasis of a tumor. As used herein, the term "inhibit" means that the amount of tumor growth or metastasis and/or the occurrence of angiogenesis in patients that have received a compound, as described herein, may be desirably reduced as compared to patients that have not received that compound. Thus, in one form, the inhibitory methods of the present disclosure comprise administering to a patient an effective amount of an anti-angiogenic agent. The term "anti-angiogenic agent", as used herein, refers to compounds which may inhibit angiogenesis.

In other embodiments, the disclosure is directed to methods for treating a disease or disorder associated with angiogenesis. These methods may include the step of identifying a patient having such a disease, including patients who would benefit from the treatment methods described herein. Diseases or disorders associated with angiogenesis include, for example, conditions in which angiogenesis plays a role in the pathology or progression of the condition, such that inhibition of angiogenesis in a patient having such a condition may delay or prevent the further progression of the condition, or lead to remission or regression of the disease state. Such conditions are frequently characterized by or associated with abnormal cellular proliferation and include, for example, neoplastic diseases. As used herein, the term "treating a disease or disorder" refers to the administration of agents intended to limit the extent, progression and/or severity of a condition in a patient, as compared to patients that have not been so treated. As used herein, the term "neoplastic disease" refers to any condition characterized by the presence of an aberrant growth of abnormal cells or tissue, including, but not limited to all cancers and tumors, whether benign or malignant. "Treating neoplastic disease" refers to the administration of a chemotherapeutic agent that will inhibit the further growth or metastasis of any neoplastic tissue that may exist in a patient and/or stimulate regression of such neoplasms, including reducing the size and/or number of such neoplasms and/or inducing the death of neoplastic cells.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynl, cycloalkyl or cycloalkenyl groups as defined earlier.

(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO$_2$R) or —NHCR(=CHCONR$_2$)
(e) Schiff Bases, —N=CR$_2$
(f) Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels. Another prodrug derived from a carboxylic acid form of the invention may be a quaternary salt type

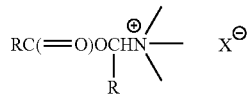

of structure described by Bodor et al., J. Med. Chem. 1980, 23, 469.

It is of course understood that the compounds of the present invention relate to all optical isomers and stereo-isomers at the various possible atoms of the molecule.

Pharmaceutically acceptable salts of the compounds of the present invention include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

The compounds of the present invention can be synthesized by persons skilled in the art once aware of the present disclosure without undue experimentation. Procedures are available in the chemical literature suitable for preparing the requisite sugars or nucleosides. Along these lines, see Choi, Jong-Ryoo; Kim, Jeong-Min; Roh, Kee-Yoon; Cho, Dong-Gyu; Kim, Jae-Hong; Hwang, Jae-Taeg; Cho, Woo-Young; Jang, Hyun-Sook; Lee, Chang-Ho; Choi, Tae-Saeng; Kim, Chung-Mi; Kim, Yong-Zu; Kim, Tae-Kyun; Cho, Seung-Joo; Kim, Gyoung-Won PCT Int. Appl. (2002), 100 pp. WO 0257288 A1 20020725. Holy, Antonin; Votruba, Ivan; Tloustova, Eva; Masojidkova, Milena. Collection of Czechoslovak Chemical Communications (2001), 66(10), 1545-1592. Rejman, Dominik; Masojidkova, Milena; De Clercq, Eric; Rosenberg, Ivan Nucleosides, Nucleotides & Nucleic Acids (2001), 20(8), 1497-1522; Ubasawa, Masaru; Sekiya, Kouichi PCT Int. Appl. (2001), 39 pp WO 0164693 A1 20010907. Otmar, Miroslav; Masojfdkova, Milena; Votruba, Ivan; Holy, Antonin. Collection of Czechoslovak Chemical Communications (2001), 66(3), 500-506. Michal; Hocek, Michal; Holy, Antonin. Collection of Czechoslovak Chemical Communications (2000), 65(8), 1357-1373. Jeffery, A. L.; Kim, J.-H.; Wiemer, D. F. Tetrahedron (2000), 56(29), 5077-5083. Holy, Antonin; Guenter, Jaroslav; Dvorakova, Hana; Masojidkova, Milena; Andrei, Graciela; Snoeck, Robert; Balzarini, Jan; De Clercq, Erik. Journal of Medicinal Chemistry (1999), 42(12), 2064-2086. Janeba, Zlatko; Holy, Antonin; Masojidkova, Milena. Collection of Czechoslovak Chemical Communications (2001), 66(9), 1393-1406. Holy, Antonin; Guenter, Jaroslav; Dvorakova, Hana; Masojidkova, Milena; Andrei, Graciela; Snoeck, Robert; Balzarini, Jan; De Clercq, Erik. Journal of Medicinal Chemistry (1999), 42(12), 2064-2086. Dang, Qun; Erion, Mark D.; Reddy, M. Rami; Robinsion, Edward D.; Kasibhatla, Srinivas Rao; Reddy, K. Raja. PCT Int. Appl. (1998), 126 pp WO 9839344 A1 19980911. Arimilli, Murty N.; Cundy, Kenneth C.; Dougherty, Joseph P.; Kim, Choung U.; Oliyai, Reza; Stella, Valentino J. PCT Int. Appl. (1998), 74 pp WO 9804569. Sekiya, Kouichi; Takashima, Hideaki; Ueda, Naoko; Kamiya, Naohiro; Yuasa, Satoshi; Fujimura, Yoshiyuki; Ubasawa, MasaruJournal of Medicinal Chemistry (2002), 45(14), 3138-3142. Ubasawa, Masaru; Sekiya, Kouichi; Takashima, Hideaki; Ueda, Naoko; Yuasa, Satoshi; Kamiya, Naohiro. Eur. Pat. Appl. (1997), 56 pp EP 785208 A1 19970723. Hocek, Michal; Masojidkova, Milena; Holy, Antonin, Collection of Czechoslovak Chemical Communications (1997), 62(1), 136-146. Holy, Antonin; Votruba, Ivan; Tloustova, Eva; Masojidkova, Milena. Collection of Czechoslovak Chemical Communications (2001), 66(10), 1545-1592. Holy, Antonin; De Clercq, Erik Desire Alice. PCT Int. Appl. (1996), 57 pp. WO 9633200 A1 19961024. Rejman, Dominik; Rosenberg, Ivan. Collection of Czechoslovak Chemical Communications (1996), 61(Spec. Issue), S122-S123. Holy, Antonin; Dvorakova, Hana; Jindrich, Jindrich; Masojidkova, Milena; Budesinsky, Milos; Balzarini, Jan; Andrei, Graciella; De Clercq, Erik. Journal of Medicinal Chemistry (1996), 39(20), 4073-4088. Guanti, Giuseppe; Merlo, Valeria; Narisano, Enrica. Tetrahedron (1995), 51(35), 9737-46. Takashima, Hideaki; Inoue, Naoko; Ubasawa, Masaru; Sekiya, Kouichi; Yabuuchi, Shingo Eur. Pat. Appl. (1995), 88 pp. EP 632048 A1 19950104. Alexander, Petr; Holy, Antonin; Masojidkova, Milena, Collection of Czechoslovak Chemical Communications (1994), 59(8), 1853-69. Alexander, Petr; Holy, Antonin; Masojidkova, Milena; Collection of Czechoslovak Chemical Communications (1994), 59(8), 1853-69. Jindrich, Jindrich; Holy, Antonin; Dvorakova, liana. Collection of Czechoslovak Chemical Communications (1993), 58(7), 1645-67. Holy, Antonin. Collection of Czechoslovak Chemical Communications (1993), 58(3), 649-74. Guanti, Giuseppe; Merlo, Valeria; Narisano, Enrica; Tetrahedron (1995), 51(35), 9737-46. Emishetti, Purushotham; Brodfuehrer, Paul R.; Howell, Henry G.; Sapino, Chester, Jr. PCT Int. Appl. (1992), 43 pp. WO 9202511 A1 19920220. Glazier, Arnold. PCT Int. Appl. (1991), 131 pp. WO 9119721. Kim, Choung Un; Luh, Bing Yu; Misco, Peter F.; Bronson, Joanne J.; Hitchcock, Michael J. M.; Ghazzouli, Ismail; Martin, John C Journal of Medicinal Chemistry (1990), 33(4), 1207-13. Rosenberg, Ivan; Holy, Antonin; Masojidkova, Milena. Collection of Czechoslovak Chemical Communications (1988), 53(11B), 2753-77. Rosenberg, Ivan; Holy, Antonin; Masojidkova, Milena. Collection of Czechoslovak Chemical Communications (1988), 53(11B), 2753-77.

The following non-limiting examples illustrate and describe aspects of the present disclosure. The examples show and describe only limited embodiments but it is to be understood that the disclosure is capable of use in various other combinations, modifications, and environments and is capable of changes or modifications within the scope of the concept as expressed herein, commensurate with the teachings and/or the skill or knowledge of the relevant art.

EXAMPLE 1

Cell Proliferation Assay

Human primary cell lines, arterial endothelia, such as HAEC and HPAEC, venous endothelia HUVEC (from Cambrex BioScience Rockland Inc.), and lung fibroblasts LL47 (from the American Type Culture Collection) are cultured by following the instruction and used to evaluate the target compounds for their differential activity against human endothelia verses fibroblasts by CellTiter-Glo Luminescent Cell viability Assay. This assay, generating luminescent signals, is based on quantification of ATP levels in cell cultures. Amount of ATP produced in cell culture reflects the number of viable cells. Hence, this assay is often used to estimate cell proliferation and cytotoxic effects of test compounds. Cells are seeded in 96-well plates with their growth medium, about $5 \times 10^3$ cell per well. After 24 hours, various doses of the target compounds are added to the cultures, having four replicates for each dose. After 72 hours of treatment, CellTiter-Glo reagent is added to the cultures following the manufacturer's instruction and luminescence is measured. The control groups are given DMSO vehicle only. $IC_{50}$s of target compounds for endothelia and fibroblasts proliferation in their growth medium are determined based on the dose response curve and plotted against the range of concentrations.

EXAMPLE 2

Endothelial Cell Migration Assay

Endothelial cell migration is a key step of the angiogenesis process, which is crucial for on-site recruitment of blood vessel formation. The trans-well filter/inserts chamber of Biocoat Endothelial Cell Migration Angiogenesis System (BD Biosciences) is used for endothelial cell migration assay, which is a 24-Transwell chamber plate containing 3-µm pore size inserts coated with human fibronectin. The inserts are incubated at 37° C. with 0.1% bovine serum albumin containing endothelial cell basal medium for 1 hour. Endothelial cells (HUVEC) are starved with 0.1% bovine serum albumin in endothelial cell basal medium for 4 to 5 hours before the cell harvest and then seeded ($1 \times 10^5$ per well) in upper chambers of the Transwell plate with various treatments in 100 ul of 0.1% bovine serum albumin in endothelial cell basal medium. The full growth medium that contains various chemoattractants is added in the lower chambers. The cells are allowed to migrate for 22±1 hours at 37° C. Unmigrated cells at the inside of the inserts are carefully removed with a Q-tip. Migrated cells at the lower part of the Transwell inserts are then fixed with 4% paraformaldehyde, stained with Hoechst 33342, and photographed under a fluorescent microscope. Three microscopic view fields of each filter/insert are analyzed for the number of migrated cells. Triplicate filter/insert chamber cultures are carried for each test concentration and control. Data are expressed as average number of migrated cells per microscopic view field of 10× magnification and $IC_{50}$ are calculated based on the dose curve.

EXAMPLE 3

Endothelial Tube Formation Assay

Human endothelial cells are cultured in vitro on extracellular matrix, which stimulates the attachment and differentiation of endothelial cells into tubules. The endothelial tube formation assay is based on this phenomenon. Endothelial cells (HUVEC) are seeded ($1.5 \times 10^4$ per well) in a 96-well plates coated with extracellular matrix and treated with the target compounds at different concentrations with the full growth medium in triplicate. The cells are allowed to form endothelial tubes at 37° C. for about 18 hours and photographed under an inverted light microscope. The tubule lengths are quantified using image analysis software, Image-Pro Plus (Media Cybernetics, Inc., Silver Spring, Md.). Data are expressed as average tube lengths of three view fields for each well and triplicate wells for each treatment condition. $IC_{50}$ values are calculated based on the dose curve.

EXAMPLE 4

Chick Chorioallantoic Membrane (CAM) Assay

Chicken embryo chorioallantoic membrane provides an ideal in vivo model for the physiologic process of angiogenesis. Angiogenic modulators applied on methylcellulose discs placed on top of chicken embryo chorioallantoic membrane are able to alter the development of new blood vasculature. See Staton et al, *Current Methods for Assaying Angiogenesis in vitro and in vivo*, INT. J. EXP. PATHOL., 85:233-48 (2004), which is incorporated herein by reference in its entirety. The angiogenesis chorioallantoic membrane assay is used for ex vivo evaluation of the anti-angiogenic potential of synthetic compounds. Fertilized chicken eggs are incubated at 37.5° C. in a humidified egg incubator with forced air circulation. On embryo Day 3, eggs are cracked open and embryos are transferred into 100-mm³ Petri plates to continue their development in a cell culture incubator at 37.5° C. Pre-made methylcellulose discs in about 2 mm in diameter are gently implanted on top of embryo chorioallantoic membrane on embryonic Day 5 and then testing compound in solution or control vehicle is applied on top of methylcellulose disc. The embryos are incubated for two more days in the cell culture incubator. The chorioallantoic membranes are examined and quantitatively analyzed for new blood vessel formation at embryonic Day 7. The treatment effects on angiogenesis are evaluated by determining vascular density index (VDI) of each CAM with viable chicken embryos. The VDI represents the number of intersections made by blood vessels with three equidistant concentric circles on the area covered by methylcellulose discs by using Image Pro Plus software. The data are expressed as average VDI based on the quantitative analysis for each treatment group (N≧5) with stander deviation.

EXAMPLE 5

Matrigel Plug Assay in Mouse

The Matrigel Plug Assay is an in vivo new blood vessel formation assay, which is widely used for evaluation of anti-angiogenic activities of synthetic compounds and recombinant proteins. Female C57BL/6 mice around 8-10 weeks old and High Concentration Matrigel Matrix is used for the Matrigel Plug experiments. There are four or five mice in each treatment group and two Matrigel plugs in each mouse. Matrigel is mixed with 50 ng/ml VEGF, 50 ng/ml FGFb, and 3 ng/ml heparin as angiogenic stimuli. Target compounds in different dosages are either mixed with Matrigel or given by i.p. or i.v. or by oral. Matrigel at 4° C. is subcutaneously injected, 500 ul Matrigel for each plug, into each sides of mouse where the hair has been shaved. The injected Matrigel will rapidly form a single solid gel plug. Plugs from each group are collected about two weeks after the Matrigel inoculation. Mice are euthanized by inhalation of $CO_2$ and mouse skin is pulled back to expose the plug. The intact plugs are removed and fixed in 10% formalin for histological analysis. Sections (5 um thickness) of paraffin-embedded plugs are immunostained with specific antibody against CD31 and counterstained with H&E. CD31-positive microvessels in an entire cross sectional area of each Matrigel plug are counted. For each group of mice, about six Matrigel plugs are quantitatively analyzed to assess any statistical significant difference of microvessel density between control and compound treated groups.

EXAMPLE 6

Anti-tumor Efficacy of Compounds Evaluated by Xenograft Nude Mouse Model

Tumor growth depends on angiogenesis. Inhibition of tumor angiogenesis has become an effective treatment for cancers. Standard Xenograft nude mouse models are used to evaluate potential anti-angiogenic agents for their anti-tumor activity. Human tumor cells or fragments are implanted into 5 to 7-weeks old nude mice. Target compounds are given to each group of mice by i.p., or i.v., or oral. Tumor size and mouse body weight are monitored twice a week. Average tumor volumes at each time points are expressed with standard deviation against tumor growth time, which is days after xenograft inoculation.

Procedures such as those described in the above examples were employed to give the data presented in the Figures and in Table I below.

well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 60 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

TABLE I

| Compound | $IC_{50}$ (μM) Arterial Endothelia Proliferation | $IC_{50}$ (μM) Venous endothelia Proliferation | $IC_{50}$ (μM) Fibroblasts Proliferation | Inhibition in Endothlial migration | | Inhibition in Endothlia Tube-Formation | | Inhibition in CAM Assay |
|---|---|---|---|---|---|---|---|---|
| | | | | 2 μM | 8 μM | 2 μM | 8 μM | (10 μg) |
| Ritanserin | 11.0 | 10.5 | >50 | 55% | 65% | 11% | 33% | 21% |
| Amiodarone hydrochloride | 7.5 | 8.8 | 20.0 | 36% | 38% | 33% | 33% | 27% |
| Terfenadine | 3.0 | 5.5 | 7.0 | 34% | 100% | 20% | 43% | 28% |
| Clomipramine hydrochloride | 10.8 | 4.5 | 28.0 | 58% | 63% | 12% | 26% | 19% |
| Perphenazine | 4.2 | 11.1 | 10.8 | 43% | 46% | 7% | 22% | — |
| Bithionol | 2.0 | 6.0 | 10.5 | 5% | 100% | 19% | 38% | 30% |

Formulations

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents such as interferon (IFN), interferon α-2a, interferon α-2b, consensus interferon (CIFN), ribavirin, amantadine, remantadine, interleukine-12, ursodeoxycholic acid (UDCA), and glycyrrhizin.

The pharmaceutically acceptable carriers described herein, for example, vehicles, adjuvants, excipients, or diluents, are Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as polyethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art (5, 6). See Banker and Chalmers PHARMACEUTICS AND PHARMACY PRACTICE, 238-250 (LB. Lippincott Co., Philadelphia, Pa. Eds. 1982) and Toissel, ASHP HANDBOOK ON INJECTABLE DRUGS, 622-630 (4th ed. 1986), which are incorporated herein by reference in its entirety.

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicates to be incorporated by reference.

The invention claimed is:

1. A method for inhibiting the growth or metastasis of a solid tumor comprising administering a therapeutically effective amount of bithionol to a patient in need thereof and inhibiting the growth or metastasis of the solid tumor.

2. The method of claim 1, wherein the administration of bithionol inhibits the growth of the solid tumor.

3. The method of claim 1, wherein the administration of bithionol inhibits metastasis of the solid tumor.

* * * * *